US012753432B2

(12) United States Patent
Kramer et al.

(10) Patent No.: US 12,753,432 B2
(45) Date of Patent: Oct. 6, 2026

(54) ASSAY METHODS AND KITS FOR DETECTING RARE SEQUENCE VARIANTS

(71) Applicant: Rutgers, The State University of New Jersey, New Brunswick, NJ (US)

(72) Inventors: Fred R. Kramer, Riverdale, NY (US); Diana Vargas-Gold, Millburn, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 907 days.

(21) Appl. No.: 17/754,032

(22) PCT Filed: Oct. 1, 2020

(86) PCT No.: PCT/US2020/053674

§ 371 (c)(1),
(2) Date: Mar. 22, 2022

(87) PCT Pub. No.: WO2021/067527

PCT Pub. Date: Apr. 8, 2021

(65) Prior Publication Data

US 2022/0333183 A1 Oct. 20, 2022

Related U.S. Application Data

(60) Provisional application No. 62/909,483, filed on Oct. 2, 2019.

(51) Int. Cl.
*C12Q 1/6853* (2018.01)
*C12Q 1/6851* (2018.01)
*C12Q 1/6876* (2018.01)

(52) U.S. Cl.
CPC ......... *C12Q 1/6853* (2013.01); *C12Q 1/6851* (2013.01); *C12Q 1/6876* (2013.01); *C12Q 2600/156* (2013.01); *C12Q 2600/16* (2013.01)

(58) Field of Classification Search
CPC .. C12Q 1/6853; C12Q 1/6851; C12Q 1/6844; C12Q 1/6858; C12Q 1/686; C12Q 2535/125; C12Q 2561/113; C12Q 2525/301; C12Q 2531/113; C12Q 2537/143; C12Q 2565/1015; C12Q 2525/161; C12Q 2525/197
See application file for complete search history.

(56) References Cited

U.S. PATENT DOCUMENTS

2013/0323727 A1* 12/2013 Huang ................. C12Q 1/6886 536/25.3
2014/0274786 A1* 9/2014 McCoy ................ C12Q 1/6844 506/9
2016/0258010 A1* 9/2016 Panousis .............. C12Q 1/6858
2018/0355420 A1 12/2018 Chen et al.
2019/0225999 A1 7/2019 Marras et al.

FOREIGN PATENT DOCUMENTS

CN 103459612 A 12/2013
CN 109312398 A 2/2019
CN 110195097 A 9/2019
JP 2002-101889 A 4/2002
JP 2019510501 A 4/2019
WO 2014/124290 A1 8/2014
WO 2017/176852 A1 10/2017

OTHER PUBLICATIONS

Tsourkas et al. Structure-function relationships of shared-stem and conventional molecular beacons. Nucleic Acids Research 2002; 30: 4208-4215. (Year: 2002).*

Kramer, F.R. and Vargas, D.Y.SuperSelective primer pairs for sensitive detection of rare somatic mutations. Scientific Reports 2021 ; 11: 22384. (Year: 2021).*

Uchibori et al. Brigatinib combined with anti-EGFR antibody overcomes osimertinib resistance in EGFR-mutated non-small-cell lung cancer. Nature Communications 2017; 8: 14768. (Year: 2017).*

Vargas, et al: "Multiplex Real-Time PCR Assays that Measure the Abundance of Extremely Rare Mutations Associated with Cancer", PLOS ONE, May 31, 2016, vol. 11, No. 5, XP093064547, DOI: 10.1371 /journal.pone.0156546. Retrieved from the Internet: <URL:https://www.ncbi.nlm.nih.gov/pmc/articles/PMC4887114/pdf/pone.0156546.pdf>.

Vargas, et al: "Suppression of Wild-Type Amplification by Selectivity Enhancing Agents in PCR Assays that Utilize SuperSelective Primers for the Detection of Rare Somatic Mutations", The Journal Of Molecular Diagnostics, Jul. 1, 2018, vol. 20, No. 4, pp. 415-427, XP055720766, ISSN: 1525-1578, DOI: 10.1016/j.jmoldx.2018.03.004.

Search Report and Written Opinion issued in Signapore Patent Application No. 11202202397Y dated May 31, 2024 (11 pages).

* cited by examiner

*Primary Examiner* — Angela M. Bertagna

(74) *Attorney, Agent, or Firm* — FOX ROTHSCHILD LLP

(57) ABSTRACT

This invention relates to methods for analyzing nucleic acids. The disclosure provides methods of a primer-dependent amplification and detection method that is capable of amplifying and detecting in a sample as few as ten copies of at least one rare intended target sequence in the presence of abundant closely related unintended target sequences. Also provided are reaction compositions and kits for performing the methods.

11 Claims, 13 Drawing Sheets

Specification includes a Sequence Listing.

**SuperSelective Primer Pair For Detection of an *EGFR* G719C Mutation**

SuperSelective Primer Pair For Detection of an *EGFR* T790M Mutation

**SuperSelective Primer Pair For the Detection of Two Different *EGFR* Mutations (T790M and C797S) Located 20 Nucleotides Apart (in *cis*) on the Same Chromosome**

**SuperSelective Forward Primer for the Detection of *EGFR* T790M and an ARMS Reverse Primer for the Detection of *EGFR* C797S**

Determination of Whether Two *EGFR* Mutations (T790M and C797S) are Present in *cis* on the Same Chromosome or are Present in *trans* on Two Sister Chromosomes

Figure 10

**ARMS Forward Primer and a SuperSelective Reverse Primer for the Detection of *KRAS* G12D in the Presence of 10,000 *KRAS* Wild-type Templates**

ARMS Forward Primer and a SuperSelective Reverse Primer

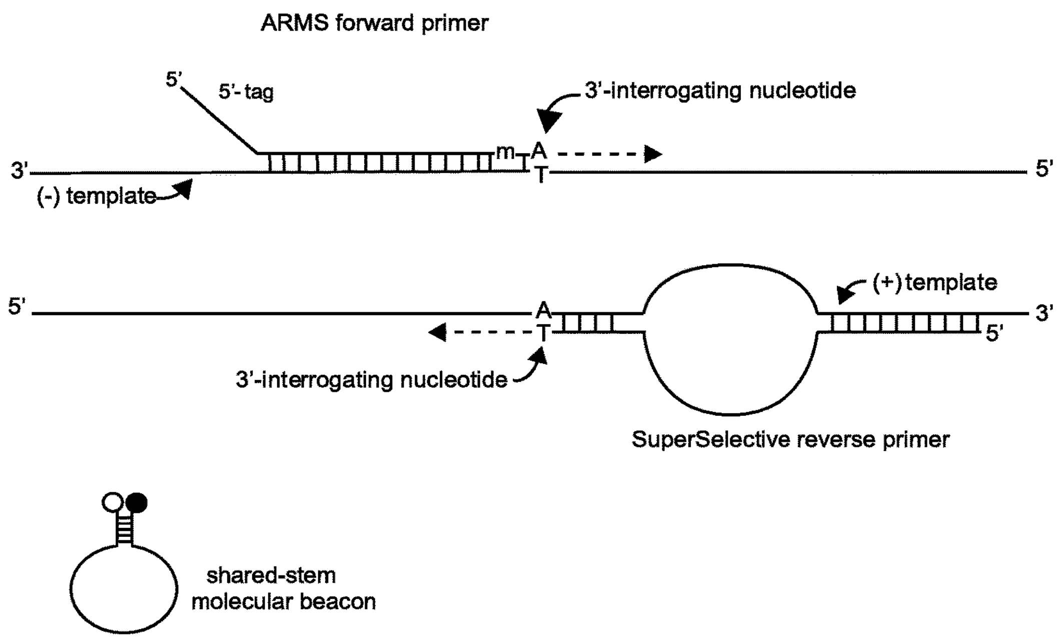

Non-Symmetric Exponential Amplification Results in Excess (-) Amplicons
(60 nM ARMS Forward Primer and 300 nM SuperSelective Reverse Primer)

Shared-stem Molecular Beacon Binds to the Complement of the ARMS Forward Primer Tag Sequence Incorporated into the 3' end of the Excess (-) Amplicons

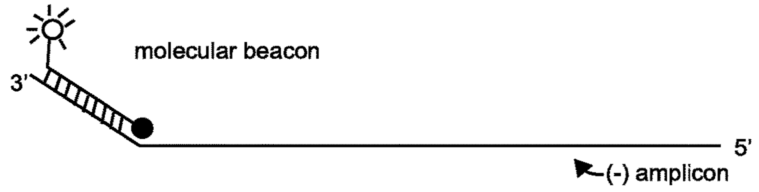

**SuperSelective Primer Pair for the Selective Amplification of *EGFR* G719C Mutant DNA Fragments in the Presence of Abundant Normal Human Genomic DNA Fragments**

Demonstration of the Selectivity and Sensitivity of an Assay that Utilizes a Pair of SuperSelective PCR Primers for the Amplification of Rare Mutant DNA Fragments in the Presence of Abundant Human Genome Fragments

ASSAY METHODS AND KITS FOR DETECTING RARE SEQUENCE VARIANTS

CROSS REFERENCE TO RELATED APPLICATION

The present application is the U.S. National Phase of International Patent Application Serial No. PCT/US20/53674, filed Oct. 1, 2020, which claims priority to U.S. Provisional Application No. 62/909,483 filed on Oct. 2, 2019. The entire disclosures of the applications noted above are incorporated herein by reference.

BACKGROUND

It has been a long sought goal to be able to detect and quantitate the presence of an extremely rare nucleic acid sequence variant in a sample containing abundant quantities of a closely related sequence; for example, detecting a rare (ten in 10,000 or less) somatic mutant sequence that occurs in cancer cells in a clinical sample (typically 10,000 or 100,000 cells) containing abundant copies of the wild-type sequence from normal cells. Next generation sequence analysis has been employed to achieve this goal, but since extensive amplification of the nucleic acids in the sample is required, and since the nucleic acid polymerase occasionally incorporates an incorrect nucleotide (creating a mutant sequence that was not present in the original sample), the sensitivity of sequencing approaches is limited. Also, sequence analysis requires expensive equipment, is slow (several days), and is expensive, costing approximately $4,000 per assay.

Various designs of allele-discriminating primers have been employed in exponential amplification assays in the hope of selectively initiating amplification on one or more rare nucleic acid variants, while ignoring the abundant closely related wild-type nucleic acids. These designs have in common that they include at least one nucleotide, that we refer to as an interrogating nucleotide, that is complementary to an intended target sequence but is mismatched to a closely related unintended target sequence. They include: hairpin-shaped primers (published international patent application WO 2000/71562 (30 Nov. 2000) and corresponding U.S. Pat. No. 6,365,729); Amplification Refractory Mutation System ("ARMS") primers (Newton et al. (1989) Nucleic Acids Research 17: 2503-2516; Kwok et al. (1990) Nucleic Acids Research 18:999-1005); and multi-part primers containing an internal sequence that is not complementary to the target sequence sandwiched between two target-complementary sequences. Multi-part primers include our own laboratory's very highly selective SuperSelective primers for closely related alleles disclosed in published international patent applications WO 2014/124290 (14 Aug. 2014) and WO 2017/176852 (12 Oct. 2017), and in U.S. Pat. No. 9,909,159. Allele-discriminating primers have in common the inclusion of an interrogating nucleotide that is complementary to the intended rare target sequence but mismatched to the unintended abundant closely related sequence.

SuperSelective primers are quite selective (see, for example, Vargas et al. (2016) PLoS ONE 11:e0156546 and Vargas et al. (2018) Journal of Molecular Diagnostics 20:415-427), rarely copying abundant closely related strands. It is especially desirable to ensure that when analyzing clinical samples that contain only a very few mutant targets (for example a sample containing ten or fewer mutant molecules in the presence of 10,000 closely related wild-type molecules) to determine without averaging multiple parallel amplifications whether the amplified signal is due to the presence of those few mutant molecules or whether the signal is the result of the unintended amplification initiated on the abundant wild-type molecules. Consequently, when performing only a single amplification, a sample containing only a very few mutant targets may occasionally be confused with a sample containing no mutant targets (resulting in a false-negative conclusion), and a sample containing no mutant targets may occasionally be confused with a sample containing only a very few mutant targets (a false-positive conclusion).

There is a significant need for an assay method to detect very rare mutations that is extremely sensitive, easy to use on existing spectrofluorometric thermal cyclers, low cost, rapid (hours rather than days), and non-invasive. The needed assay must be able to differentiate between a sample containing only an abundant nucleic acid sequence (for example, a wild-type sequence) and a sample containing as few as ten copies of a closely related rare nucleic acid sequence (for example, a mutant sequence) per 10,000 copies of the abundant nucleic acid sequence.

For assays utilizing allele-discriminating primers, there is a need for robust assay methods to detect a very few mutant target sequences in a background of abundant wild-type sequences, for example, ten mutant sequences in a mixture containing 10,000 wild-type sequences. Selectivity and sensitivity can be condensed into the single feature of being capable of detecting as few as ten copies of a rare target sequence in a mixture containing 10,000 copies of a closely related sequence differing by one or two nucleotides.

SUMMARY

This invention addresses the need mentioned above in a number of aspects.

In one aspect, the invention provides a primer-dependent amplification and detection method that is capable of amplifying and detecting in a sample as few as ten copies of at least one rare DNA intended target sequence ("rare target sequence") in a mixture containing, for each rare target sequence, 10,000 copies of a closely related unintended target sequence ("closely related sequence" or "unintended target sequence") that differs from the rare target sequence by as little as one or two base pairs. The method comprises: (a) preparing a primer-dependent amplification reaction mixture that includes the sample, a DNA polymerase, deoxyribonucleoside triphosphates, an amplification buffer, homogeneous fluorescence detection means for detecting amplification products, and for each rare target sequence a pair of primers consisting of a first primer and a second primer that are specific for the rare target sequence, but mismatched to the closely related sequence, (b) repeatedly cycling the primer-dependent amplification reaction mixture to amplify each rare target sequence present in the sample, and (c) detecting that rare target sequence by measuring the intensity of fluorescence from a homogeneous fluorescence detection means. The first primer can be an allele-discriminating multi-part primer comprising from the 5' end to the 3' end a first anchor sequence, a first bridge sequence, and a first foot sequence that is mismatched to the closely related sequence by at least its 3'-terminal or 3'-penultimate nucleotide. The second primer can be an allele-discriminating primer.

In the method, the first primer, the second primer, or both can be a SuperSelective primer that is mismatched to the closely related sequence by at least its 3'-terminal or 3'-penultimate nucleotide. Each primer can contain a 3'-terminal interrogating nucleotide that is complementary to the rare target sequence but mismatched to the unintended target sequence.

In the method described above, cycling can comprise temperature cycling in a non-symmetric polymerase chain reaction (PCR) method. In one embodiment, the detecting step can comprise real-time detection. In another embodiment, the PCR method can be a digital PCR method, and detection can comprise end-point detection.

In the method described above, the at least one rare target sequence in the sample can include at least two different rare target sequences. In that case, the homogeneous fluorescence detection means can comprise at least two different homogeneous fluorescence detection probes for the at least two different rare target sequences, respectively. The at least two rare target sequences can include a group of rare target sequences, and the probe for the rare target sequences in the group can be labeled with the same color. The probes can be color-coded.

In some embodiments, each different unintended target sequence can differ from its corresponding rare target sequence by a single base pair, and both the first and the second primers are mismatched to that single base pair. Each second primer can be a multi-part primer comprising from the 5' end to the 3' end a second anchor sequence, a second bridge sequence, and a second foot sequence. The homogeneous fluorescence detection means can comprise a probe for each rare target sequence. The first or second primer, or both the first and second primer, for each rare target sequence can contain a 5'-tag sequence, and the complement of each 5'-tag sequence is the target of a probe, or a pair of probes.

Each probe described above can comprise a sequence that is complementary to the complement of the first bridge sequence or the complement of the second bridge sequence. Examples of the probe include a shared-stem molecular beacon.

In the above-described method, the at least one rare target sequence can differ from its corresponding unintended target sequence by a first base pair and a second base pair that occur in the same gene in cis. In that case, the first primer can be complementary to the first base pair and the second primer can be complementary to the second base pair. In some embodiments, the at least one rare target sequence in the sample can include two or more rare target sequences, and the homogeneous fluorescence detection means can comprise at least one homogeneous fluorescence detection probe for each rare target sequence. Examples of the homogeneous fluorescence detection means for each rare target sequence comprise an interprimer-specific molecular beacon probe.

The above-described primer-dependent amplification reaction mixture can further include an effective amount of a selectivity-enhancing reagent, such as a Hofmeister salt. Examples include tetramethylammonium chloride (TMAC) and bis-tetramethylammonium oxalate.

The invention also provides a kit of reagents or a composition (e.g., a reaction mixture) for performing the method described above. The kit or composition can include one, two, or more of reagents selected from the group consisting of a primer described above, a nucleic acid polymerase, deoxyribonucleoside triphosphates, and a detecting agent. Examples of the detecting agent include homogeneous fluorescence detection means such as a molecular beacon probe for each rare target sequence.

Methods according to this invention utilize for each of at least one rare target sequence a pair of first and second allele-discriminating primers, at least one of which is a multi-part first primer, preferably a SuperSelective primer. Both primers in each pair of amplification primers are specific for the target sequence but mismatched to the closely related sequence. Each multi-part first primer is mismatched to the closely related sequence by at least its 3'-terminal or 3'-penultimate nucleotide. In certain preferred embodiments each allele-discriminating second primer can be as well. We prefer that in both the forward and reverse primers of each primer pair, the interrogating nucleotide is a 3'-terminal nucleotide. Methods according to this invention optionally include amplification and detection of an unrelated wild-type gene sequence for the purpose of quantitation.

The methods can be divided into two general types:

In the first type, each rare target sequence contains a single difference, for example, a mutation (as the result of a deletion, an insertion, or a nucleotide change such as a single-nucleotide polymorphism (SNP)). In the case of a SNP, the rare intended target sequence contains a single base pair that differs from the closely related sequence, as, for example, where a mutant sequence differs from a wild-type sequence by a single base pair. In that case both primers have an interrogating nucleotide specific for the differing single base pair in the rare target sequence; that is, the forward primer has a 3'-terminal or 3'-penultimate interrogating nucleotide that is complementary to the single base pair in one of the two strands of the mutant nucleic acid, and the reverse primer has a 3'-terminal or 3'-penultimate interrogating nucleotide that is complementary to the other mutant nucleotide of that base pair in the other of the two strands of the mutant nucleic acid, whereby one primer binds to a target strand, and the other primer binds to the complementary target strand. An amplification reaction mixture containing the sample is subjected to multiple cycles of a primer-dependent amplification reaction, and fluorescence is detected, either in real time or after amplification (end-point detection, which is used for digital PCR). During amplification, the nucleic acid polymerase cannot incorporate an incorrect nucleotide into an amplicon generated from an unintended target sequence (creating a mutant sequence that was not present in the original sample), because the primers only initiate synthesis beyond the site where the target mutation would be present.

The second type addresses the need to sometimes determine whether two different mutations occur on different sister chromosomes (i.e., in trans), in which case there are two different versions of the encoded protein that can be made, but each version is encoded by only one of those two mutations; or whether these two mutations are present and occur on the same chromosome (in cis), in which case the protein encoded by that gene on the mutant chromosome contains both mutations. In the second type, the rare target sequence contains two base pairs that differ from a wild-type sequence, where the base pairs occur in the same exon or in different exons, and may occur in either a cis relationship or in a trans relationship. In that type of target, the forward primer has an interrogating nucleotide specific for one of the mutations, and the reverse primer has an interrogating nucleotide specific for the other mutation. For example, the occurrence of either the T790M mutation or the C797S mutation in Exon 20 of the EGFR gene in a patient's non-small cell lung cancer introduces an amino acid substitution into the encoded EGFR protein that indicates that the first-line therapy (Gefitinib or Erlotinib) will not work, and suggests that the use of Osimertinib will be effective (Lamb and Scott (2017) Targeted Oncology 12:555-562). However, it has recently become apparent that if both the T790M mutation and the C797S mutation occur in the EGFR gene on the same chromosome (i.e., in cis), which results in two amino acid substitutions occurring in the same EGFR protein, then Osimertinib will not kill those cancer cells, and only Brigatinib will be effective (Uchibori et al. (2017) Nature Communications 18:14768). In methods of this invention to make that determination, one primer of the pair interrogates the T790M mutation in one fragment strand, the (+) strand, and the other primer interrogates the C797S mutation in the complementary strand, the (−) strand. Only a fragment containing both mutations will be amplified. Although probing the resulting amplicons can target the complement of the limiting primer's bridge sequence or the complement of the limiting primer's 5'-tag sequence, our preferred embodiments utilize a homogeneous fluorescence detection probe, preferably a molecular beacon probe, that targets the portion of the amplicon between the sequences where the two probes bind, (i.e., an interprimer-specific probe).

Methods according to this invention are highly selective, highly sensitive, and exhibit improved robustness. By highly selective is meant the ability to detect a rare sequence in a mixture with a closely related sequence when the ratio is as low as 1/1,000. By highly sensitive is meant the ability to detect as few as ten copies of the rare sequence in such a mixture. Selectivity and sensitivity can be condensed into a single requirement as the ability to detect as few as ten copies of a rare target sequence in a mixture containing 10,000 copies of a closely related sequence differing by one or two nucleotides. Published international patent applications WO 2014/124290 (14 Aug. 2014) and WO 2017/176852 (12 Oct. 2017), and U.S. Pat. No. 9,909,159) describe real-time PCR methods utilizing primer pairs consisting of a SuperSelective forward primer and a conventional reverse primer, including methods capable of detecting as few as ten copies of a rare target sequence in a mixture containing 10,000 copies of such a closely related sequence, where the difference between the threshold cycle from a sample containing only 10,000 copies of the closely related sequence differs from the threshold cycle from a sample additionally containing ten copies of the rare target sequence (ΔCt) generally by two or a few cycles, often with some variability among replicates. Methods according to this invention have improved robustness without sacrificing the foregoing selectivity and sensitivity. By "improved robustness" is meant that the method meets one of two criteria: either a sample containing only 10,000 copies of the closely related sequence does not achieve threshold florescence intensity for at least 55 amplification cycles, or the ΔCt between a sample containing only the closely related sequence and a sample additionally containing ten copies of the rare target sequence is at least five cycles greater than when the primer pair contains the same SuperSelective primer and a conventional primer.

Methods and kits according to this invention utilize, as noted above, a pair of allele-discriminating primers, each of which is complementary to a rare target sequence but mismatched to a closely related sequence differing from the rare target sequence by one or two nucleotides. A first primer in all cases is a multi-part primer, preferably a SuperSelective primer. The second primer is an allele-discriminating primer. It may be, for example, a SuperSelective primer or another multi-part primer, an allele-discriminating hairpin primer, or an ARMS primer. In embodiments of the first type, the second primer, like the first primer, contains an interrogating nucleotide at or near its 3' terminus. Multi-part primers and ARMS primers can meet that requirement, but allele-discriminating hairpin primers do not. However, embodiments of the second type do not have that requirement for the second primer, so a multi-part primer (preferably a SuperSelective primer), an ARMS primer, or an allele-discriminating hairpin primer can be used.

Assay methods according to this invention are primer-dependent amplification and detection methods. Primer-dependent amplification reactions useful in methods of this invention may be any suitable exponential amplification method, including the polymerase chain reaction (PCR), the ligase chain reaction (LCR), the nicking enzyme amplification reaction (NEAR), strand-displacement amplification (SDA), nucleic acid sequence-based amplification (NASBA), transcription-mediated amplification (TMA), and rolling circle amplification (RCA). Preferred methods utilize PCR.

Primer-dependent amplification and detection methods according to this invention can utilize non-symmetric DNA amplification, for example, asymmetric PCR. Symmetric DNA amplification can also be used, but we prefer non-symmetric amplification. In non-symmetric PCR amplification methods, one primer, the limiting primer, is present in a limiting amount so as to be exhausted prior to completion of amplification, preferably at or shortly after the threshold cycle, after which point linear amplification occurs, using the remaining primer, the excess primer. A non-symmetric PCR method useful in this invention is LATE-PCR (see, for example, European Patent EP 1,468,114; and Pierce et al. (2005) Proceedings of the National Academy of Sciences of the United States of America 102:8609-8614).

Preferred methods also include digital PCR (see, for example, Vogelstein and Kinzler (1999) Proceedings of the National Academy of Sciences of the United States of America 96:9236-9241), where a single PCR assay mixture is divided into a very large number of individual wells or droplets, such that only one target molecule (or no target molecule) is present in each well or droplet, and it is therefore desirable to detect amplicons from a single mutant template molecule that is present in individual wells or droplets that also can contain related wild-type molecules.

If the amplification reaction utilizes an RNA-dependent DNA polymerase (an example being NASBA), the amplification reaction can be isothermal. We refer to repeated rounds of synthesis of amplified product as "cycles", but with NASBA they are not thermal cycles. For such amplifications the "intended target sequence" and the "unintended target sequence" that are primed by a multi-part primer according to this invention are RNA sequences that occur in an original sample and in the amplification reaction mixture, where they are present with the DNA polymerase and the multi-part primer.

If the amplification reaction utilizes a DNA-dependent DNA polymerase (an example being PCR), an original sample may contain either DNA or RNA targets. For such amplifications, the "intended target sequence" and the "unintended target sequence" that are primed by a multi-part primer that is useful in methods of this invention are DNA sequences that either occur in an original sample or are made by reverse transcribing RNA sequences that occur in the original sample. If the multi-part primer is used for reverse transcription, the "intended target sequence" and the "unintended target sequence" are RNA as well as cDNA. If a separate, outside primer is used for reverse transcription, the "intended target sequence" and the "unintended target sequence" are cDNA. In either case, the "intended target sequence" and the "unintended target sequence" are nucleic acid sequences that are present in the amplification reaction mixture with the DNA polymerase and the multi-part primer.

Primer-dependent amplification reactions comprise repeated thermal cycles of primer annealing, primer extension, and strand denaturation (strand melting). Primer annealing may be performed at a temperature below the primer-extension temperature (for example, three-temperature PCR), or primer annealing and primer extension may be performed at the same temperature (for example, two-temperature PCR). The overall thermal profile of the reaction may include repetitions of a particular cycle, or temperatures/times may be varied during one or more cycles. For example, once amplification has begun and the priming sequence of a multi-part primer is lengthened, a higher annealing temperature appropriate for the longer primer might be used to complete the amplification reaction.

A preferred method according to this invention is a primer-dependent amplification and detection method, most preferably a non-symmetric method, that is capable of non-symmetrically amplifying and detecting in a sample as few as ten copies of at least one rare DNA intended target sequence in a mixture containing, for each rare target sequence, 10,000 copies of a closely related unintended target sequence that differs from the rare target sequence by as little as one or two nucleotides, comprising:

(a) preparing a primer-dependent amplification reaction mixture that includes the sample, a DNA polymerase, deoxyribonucleoside triphosphates, amplification buffer, homogeneous fluorescence probes for detecting amplification products, and for each rare target sequence a pair of allele-specific amplification primers specific for the target sequence, but mismatched to the closely related sequence, each primer pair including an allele-discriminating multi-part first primer that is mismatched to the closely related sequence by at least the 3'-terminal or 3'-penultimate nucleotide and an allele-discriminating second primer;

(b) repeatedly cycling the reaction mixture by said primer-dependent amplification method to amplify each rare DNA target sequence present in the sample, and detecting that sequence by measuring the intensity of fluorescence from the distinguishably labeled probe that targets its amplification product;

wherein, if said method is tested on a first sample containing 10,000 copies of the unintended target sequence and a second sample containing 10 copies of the intended target sequence in a mixture having 10,000 copies of the unintended target sequence, either (a) the fluorescence signal from the first sample is suppressed for 55 amplification cycles or (b) the threshold-cycle difference (ΔCt) between the two amplifications is at least five cycles greater than that obtained if the same test is performed wherein the second primer is replaced with a conventional primer.

If the second primer is a multi-part primer, it is mismatched to the closely related sequence by at least its 3'-terminal or 3'-penultimate nucleotide. If the second primer is an ARMS primer, it is mismatched to the closely related sequence by its 3'-terminal nucleotide. If the second primer is a hairpin primer, it is mismatched to the closely related sequence by a nucleotide in its single-stranded loop.

In the Examples set forth below, we used a typical, non-proprietary buffer that contains KCl, Tris-HCl (pH 8.0), and $MgCl_2$. The contents of some amplification buffers are considered to be proprietary by suppliers. Since such buffers are functionally equivalent, they may also be employed. In some preferred embodiments, the amplification reaction mixture includes an effective concentration of a selectivity-enhancing reagent, preferably tetramethylammonium chloride (TMAC).

In certain preferred methods, each primer contains a 3'-terminal interrogating nucleotide that is complementary to the intended target sequence but mismatched to the unintended target sequence. In some embodiments one primer of a pair of primers contains a 5'-tag sequence, and the complement of the 5'-tag sequence is the target of the probe.

Detection can be by a homogeneous detection means for detecting amplified products. The detection means may include a homogeneous detection probe, multiple homogeneous detection probes all labeled with the same color; labeled primers, for example Scorpion primers or LUX primers; or an intercalating DNA dye, for example SYBR® Green, if it is not necessary to distinguish among amplified products for multiple rare intended target sequences, such as when there is only one target or group of targets being detected or when it desired to detect only whether any of multiple targets is present. Otherwise there is a differently colored homogeneous fluorescence detection probe for each target (or group of targets) being detected. A homogeneous fluorescence detection probe may be, for example, a TaqMan® probe, a minor groove binder (MGB) probe, a molecular beacon probe, or an MNAzyme/cleavable-probe combination (WO 2013/123552). Our preferred detection is by a molecular beacon probe that targets an amplicon (amplified product) sequence that is complementary to a 5'-tag sequence that is included in the sequence of a limiting multi-part primer, or that targets an amplicon sequence that is complementary to a bridge sequence in a limiting multi-part primer.

As indicated above, functional features of such assays are (a) that they are capable of detecting as few as ten copies of each rare target sequence in the presence of 10,000 copies of its closely related abundant sequence, and (b) they have improved robustness in differentiating between (i) a sample containing only 10,000 copies of the closely related sequence and (ii) a sample containing 10,000 copies of the closely related sequence and 10 copies of the rare intended target sequence according to the following test. If reaction mixtures containing the two samples are subjected to real-time PCR utilizing the first and second primers according to this invention and also to the same method except that a conventional primer is substituted for the second, allele-discriminating primer, one of the following results is obtained: (1) for the sample containing only the closely related sequence, fluorescence does not rise above background for 55 cycles using the primer pair according to this invention, or (2) the difference in the appearance of a fluorescence signal whose intensity is above background between the two samples (ΔCt) is at least five amplification cycles greater using the primer pair of this invention than it is when the conventional primer is substituted.

Sensitivity in preferred embodiments can be improved by including in the amplification reaction mixture a selectivity-enhancing reagent, preferably tetramethylammonium chloride (TMAC) or another Hofmeister salt, disclosed in International Patent Application WO 2017/176852 (Oct. 12, 2017). This reagent can be included in the amplification reaction mixtures to improve selectivity against wild-type or other closely related unintended target sequences. Such a reagent is added at an effective concentration, as determined by trial and error. Certain preferred SuperSelective primers used in methods of this invention have relatively long feet, for example 9-11 nucleotides, and also form large bubbles of 32-48 nucleotides, often comprised of long bridge sequences in the range of 15-24 nucleotides. For reaction mixtures containing such SuperSelective primers, TMAC can be included in relatively high concentration, for example 50 mM or 60 mM. For reaction mixtures containing SuperSelective primers with shorter feet, for example 5-7 nucleotides, TMAC can be added in lesser concentration, for example 10 mM, 20 mM, or 30 mM, so as to avoid a deleterious effect on the amplification reaction. The test described in the preceding paragraph can be used to ascertain whether and how much of a selectivity-enhancing reagent is to be included in a particular reaction mixture by comparing, for example, results achieved with varying concentrations (say 0, 10 mM, 50 mM, and 60 mM) of TMAC. By "effective concentration" is meant a concentration that allows passing of the test, optimally the concentration that most improves the results of the test and does not significantly interfere with the amplification reaction.

Methods according to this invention are particularly suited for multiplexing, having the capability to amplify multiple rare target sequences that may be present in a sample. Different embodiments have different objectives and features. For example, certain multiplex embodiments can be designed to be capable of detecting in a sample containing genomic DNA fragments the presence of each of at least two mutations in the presence of an abundance of the wild-type sequence. A different primer pair may be used for each target sequence, with a uniquely colored fluorescent probe, preferably a molecular beacon probe, targeting an amplicon sequence that is not present in the probes themselves or in wild-type correctly amplified product. For methods of the first type, the target of each probe is preferably the complement of the bridge or the 5' tag of each different limiting primer. For methods of the second type, the target of each probe may also be the complement of the bridge or the 5' tag, but we prefer to use an interprimer-specific probe. Alternatively, a different primer pair may be used for each different group of target sequences where the presence of one or more mutations in a group is technically significant, for example, significant regarding treatment of a cancer patient. Monoplex and multiplex methods described above typically can be performed in a spectrofluorometric thermal cycler, which limits the number of distinguishable fluorescent labels (commonly used thermal cyclers are 5-color instruments) to a maximum of seven or sometimes ten. Reaction mixtures for assays to detect different groups of rare target sequences include a different multi-part limiting primer for each mutant target sequence, and optionally an unrelated wild-type gene sequence for the purpose of quantitation, wherein each multi-part limiting primer in a group of primers has the same 5'-tag sequence, and each group has a different 5'-tag sequence.

Methods of the second type, that is, detection of two mutations in a cis relationship, may have as a possibility that either of the two rare base pairs, or even both of them, have multiple possibilities that may even give rise to the same amino acid change. For example, there may be instances where one base pair change may be constant, but the other base pair change may be variable, say change X, change Y, or change Z, either at the same location or at slightly different locations. Where this occurs, a multiplex assay method may have an allele-discriminating primer specific for each possibility; for example, one primer specific for the constant change, but three primers specific for the variable change (one for X, one for Y, one for Z). Also, an interprimer-specific probe will signal the presence of a change, but it will not identify which change. For that purpose each of the primers (for X, Y, and Z) can have a unique 5' tag or a unique bridge whose complement will be the target of a different probe that is uniquely colored.

Yet other embodiments of multiplex assays, particularly methods of the first type, are screening assays, whose objective is to determine which mutant target sequence from a list of many different mutant target sequences is present in a sample, or to determine that none of those mutant target sequences is present in that sample. In these assays, whichever mutant target sequence is present is exponentially amplified, preferably in a polymerase chain reaction, and the resulting amplicons (which are only generated if a mutant target sequence was present in the sample) are detected with fluorescently labeled hybridization probes. In such embodiments, there is for each possible mutant target sequence a multi-part limiting primer, preferably a SuperSelective primer, each having a different 5'-tag sequence, whose complement is the target for a hybridization probe. Usually, the number of mutant target sequences on the list exceeds the number of different fluorescent colors that the detection instrument can distinguish, which can also happen with other multiplex assays. We solve this problem in either of two ways. One way is to use color-coded homogeneous detection probes, preferably color-coded molecular beacon probes disclosed in International Patent Publication WO 2004/099434 A3, U.S. Pat. No. 7,385,043, and in Marras et al. (2019) PloS ONE 14:e0213906. Briefly, a batch of a probe is divided into the number of aliquots in the coding scheme, generally two or three, and each aliquot is then labeled with a differently colored fluorophore, and the aliquots are recombined to create a batch containing a code of two or three colors. A second way to overcome the color limitations of spectrofluorometric thermal cyclers is to employ what we refer to as "thermospecific" molecular beacon probes whose probe-target hybrids have different melting temperatures (Tm's). For example, if a liquid biopsy sample is to be tested on a five-color spectrofluorometric thermal cycler for the presence of one or more of 35 different target sequences, 35 different multi-part limiting primers, each specific for a different target sequence, can be divided into five sets of seven. All seven in each of the five sets have different 5' tags whose complementary sequences are targets for seven different thermospecific molecular beacon probes, all of which are labeled with the same fluorophore, but all of which produce probe-target hybrids having distinguishable melting temperatures (Tm's). Thus, each one of the 35 different target sequences, if present, can be identified by a combination of fluorescence color and Tm determined in a post-amplification (end-point) thermal analysis.

As an alternative to assays of the first type being carried out by real-time amplification and detection assay methods, they may be carried out by digital PCR assay methods, including assays carried out in many different reaction wells in a thermal cycler, and droplet digital PCR (ddPCR) assays carried out in many different droplets in a thermal cycler. In both cases detection of the resulting amplicons following amplification (end-point detection) is often carried out in a separate detection instrument, for example the Bio-Rad QX200™ Droplet Digital PCR System or the Stilla Technologies Naica™ System. The basic principal underlying digital PCR assays is that a reaction mixture containing a sample can be diluted to such an extent that, for each rare target molecule being detected, only one target DNA molecule (rare intended target molecule or abundant unintended target molecule) is usually present in a well or droplet (or no target molecule is present in a well or droplet), and there are a large number of wells or droplets; however, some wells or droplets may contain no target molecule, two or three unintended target molecules, or an intended target molecule plus one or two unintended target molecules. Then, simultaneous PCR amplifications are carried out in each well or droplet. Fluorescently labeled probes that are present in all wells or droplets bind to the amplicons generated in each well or droplet (if it contained an intended target molecule) and become brightly fluorescent in a particular color or color code, indicating both that the well or droplet contained an intended target molecule and identifying which intended target sequence that was. Wells or droplets having a fluorescence intensity above a selected threshold intensity (background) at the completion of amplification are considered to be positive for a particular color or color code. The number of droplets or wells that light up in the same color or color code provides an accurate measure of the number of the corresponding target molecules in the original sample. This approach is so sensitive that even a single DNA fragment containing a target sequence in a well or droplet can be detected.

Classical droplet digital PCR has been used to detect and quantitate rare somatic mutations relevant to cancer diagnosis, prognosis, and therapy. See Sanmamed et al. (2015) Clinical Chemistry 61:297-304. In order to separate the rare mutant target molecules from the much more abundant related wild-type molecules, more than a million droplets are required. See, for example, Hindson et al. (2011) Analytical Chemistry 83:8604-8610. This large number of droplets is necessary because there are many more wild-type targets in a sample than the number of rare related mutant targets (which often only differ from the wild-type target by a single-nucleotide polymorphism), and because the probes (which are designed to bind to a subsequence within the amplicon that contains the mutation) occasionally bind to the corresponding sequence in the amplicons generated from the related wild-type targets, so it is desirable to have so many droplets that it is highly unlikely that a droplet that contains a mutant target will also contain one or more related wild-type targets. This assures that there will not be a droplet containing sufficient wild-type targets that the intensity of the signal generated in that droplet is similar to the intensity of the signal that would have been generated had that droplet mistakenly been considered to contain the related mutant target. Put another way, had the original sample been divided into too few droplets, then droplets containing some wild-type target sequences and no related mutant target sequence could be mistaken for droplets containing a mutant target.

However, when digital PCR embodiments employing the methods of this invention to detect rare mutant target molecules in a sample are used, far fewer droplets or wells (for example, only 10,000 to 30,000 droplets) are needed, because the primer pairs used do not generate detectable amplicons from the relatively few closely related wild-type DNA molecules that may also be present in a well or droplet. In digital PCR assays methods according to this invention, detection may occur in a thermal cycler, in a flow cytometer, or with a microscope, as well as in one of the detection instruments described above.

This invention also includes reagent kits for performing the foregoing methods. Such kits can include one or more pairs of allele-specific primers for one or more intended rare target sequence, dNTPs, a primer-dependent polymerase, a detection probe for each intended rare target sequence (or for a group of rare target sequences in some embodiments) and other reagents, particularly amplification buffer, needed for amplification. One primer of each primer pair can be a multi-part primer, and the other primer of each pair can be a SuperSelective or other multi-part primer, or an ARMS primer.

The selectivity of a SuperSelective primer can be maximized for a particular target by adjusting the foot length and the bubble circumference, where, in general, larger bubbles and shorter feet increase selectivity. Also, by adjusting the length and nucleotide sequence of the bridge sequence, a SuperSelective primer can be fine-tuned for maximum discrimination, and can be fine-tuned to assure that a given Ct value for any pair of primers in the same assay reflects the same number of nucleic acid targets in the sample).

BRIEF DESCRIPTION OF THE FIGURES

FIG. 10 depicts the design of the method of Example 5 for detecting rare copies of a mutation utilizing an ARMS forward primer complementary to the mutation and SuperSelective reverse primer complementary to the mutation, with detection by a molecular beacon probe targeting the complement of a 5'-tag on the ARMS forward primer.

FIGS. 11A, 11B, and 110 show the results of the real-time PCR assays of Example 5, wherein top panel A shows amplification and detection utilizing a pair of SuperSelective primers; bottom left-hand panel B shows amplification and detection utilizing a limiting SuperSelective forward primer and an excess ARMS reverse primer; and bottom right-hand panel C shows amplification and detection utilizing a limiting ARMS forward primer and an excess SuperSelective reverse primer, where in all three cases both primers are complementary to a single mutant base pair in the intended target sequence.

DEFINITIONS AND NOMENCLATURE

Figure 1:
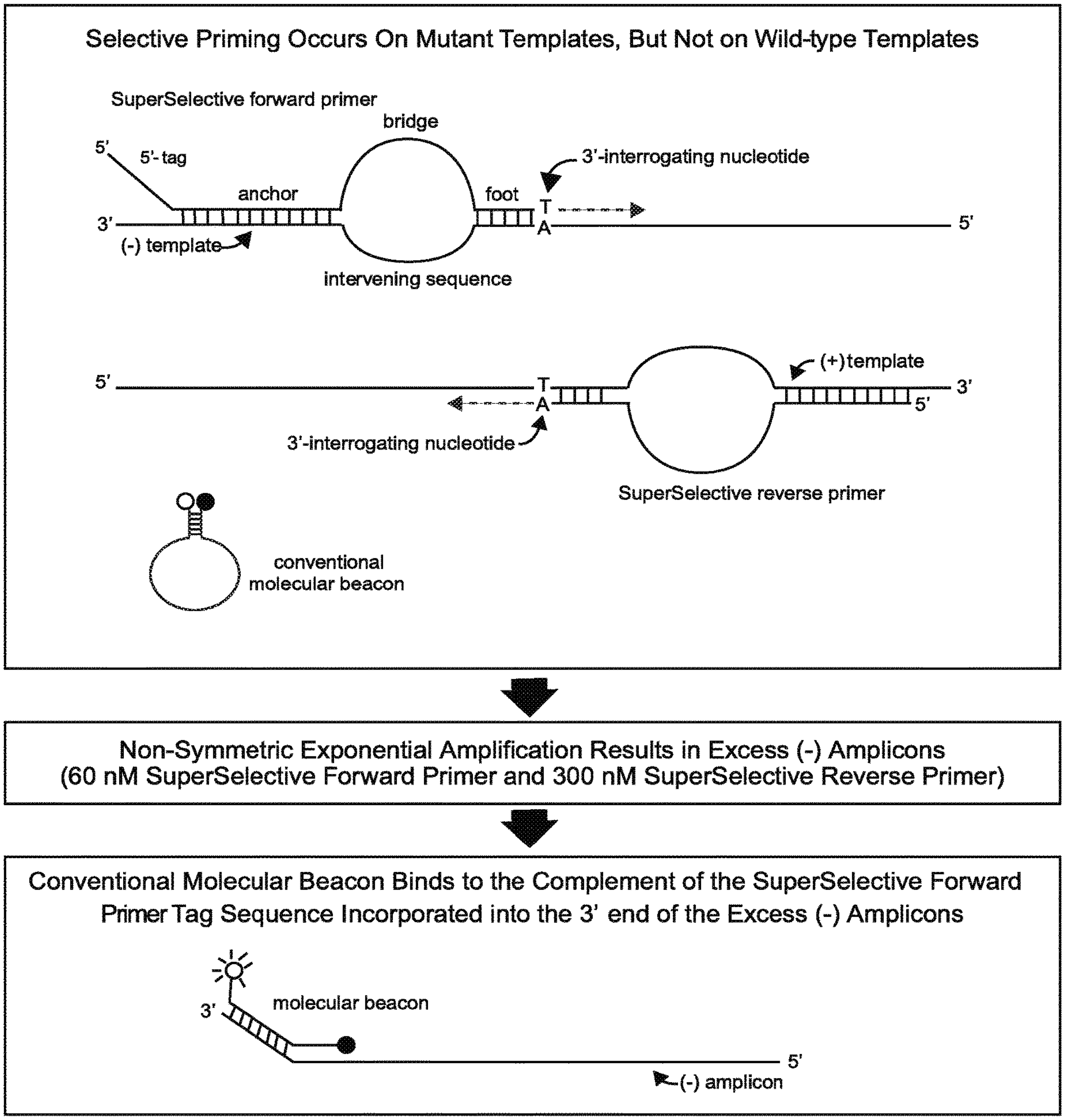
FIG. 1 depicts the design of the method of Example 1 for detecting rare copies of a mutation utilizing a pair of SuperSelective primers complementary to the mutation, with detection by a molecular beacon probe targeting the complement of a 5'-tag on the limiting SuperSelective primer.

As used in this description and in the claims of the instant patent application, the following definitions apply:

An allele-discriminating "multi-part primer" means a nucleic acid (e.g., DNA) amplification primer that has an internal sequence, which we call a "bridge sequence", that is not sufficiently complementary to the target sequence to hybridize therewith under primer-annealing conditions and that is sandwiched between two target-complementary sequences that we call an "anchor sequence" and a "foot sequence". An anchor sequence, like a conventional primer, has sufficient complementarity to the target sequence (both the intended target sequence and the unintended target sequence) to hybridize therewith during the primer-annealing step of the primer-dependent amplification reaction for which the primer is designed, typically 15-40 (e.g., 17-35, or 20-30) complementary nucleotides. The foot sequence is sufficiently complementary to the rare intended target sequence (for example, a mutant sequence) to hybridize thereto during primer annealing when the anchor sequence hybridizes so as to initiate copying, but mismatched to the abundant closely related unintended target sequence (for example, a wild-type sequence) in at least one of its 3' terminal and 3' penultimate nucleotides. We refer to a nucleotide that is complementary to the intended target sequence but mismatched to the closely related unintended target sequence as an "interrogating nucleotide". A foot sequence may include a deliberately introduced nucleotide near its 3' end that is mismatched both to the intended target sequence and to the unintended target sequence to destabilize the foot and increase its allele discrimination. A foot sequence typically can have 5-12 (e.g., 5-10, 6-12, 6-9, or most preferably 8-9) nucleotides that are complementary to the intended target sequence. The bridge sequence may be anywhere from 1-50 (e.g., 5-40, 10-30, 15-30, 20-30, or most often 18-22 or 10-14) nucleotides in length. When a multi-part primer is hybridized to its target sequence, there is in the target sequence, opposite the bridge sequence, a region not hybridized to the bridge that we call an "intervening sequence" that may be anywhere from 1-100 nucleotides in length. Together, the bridge sequence and the intervening sequence create a "bubble" in the primer-target hybrid whose circumference, ignoring any secondary structures, is the sum in nucleotides of the length of the bridge sequence and the length of the intervening sequence plus four nucleotides.

A "SuperSelective" primer is an allele-discriminating multi-part primer structured so that it enables the detection of as few as ten copies of a rare target sequences in the presence of 10,000 copies of a closely related sequence that differs by as little as a single base pair when said primer is used as the limiting primer in a PCR amplification. A SuperSelective primer has a sequence comprising, in the 5' to 3' direction, the following three contiguous nucleic acid sequences (e.g., DNA sequences) that are copied by extension of the other primer:

- an anchor sequence that is sufficiently long so that it is able to hybridize with the mutant or otherwise closely related DNA target sequences and with the related wild-type or otherwise abundant DNA target sequence during primer annealing, typically a length in the range of 15-40 nucleotides, often 20-30 nucleotides;
- a unique bridge sequence at least six nucleotides long that does not hybridize during primer annealing to the primer's intended target sequence or to any other closely related sequence; and
- a unique foot sequence that can be 6 to 12 nucleotides long and that is perfectly complementary to the intended DNA target sequence but mismatches a closely related sequences by one or more nucleotides (interrogating nucleotide or nucleotides), at least one of which is the 3'-terminal nucleotide or the 3'-penultimate nucleotide.

A SuperSelective primer may also have one or more of the following structural and functional characteristics in a polymerase chain reaction (PCR) amplification and detection assay:

(i) if the anchor sequence and the foot sequence are both hybridized to the primer's intended target sequence, the primer-target hybrid comprises in the 5' to 3' direction of the primer: an anchor-target hybrid, a single-stranded bubble, and a foot-target hybrid, said bubble having a circumference of 18 to 50 nucleotides and being formed by an intervening sequence in the target DNA sequence that is at least eight-nucleotides long and does not hybridize to the bridge sequence during primer annealing;

(ii) the bubble isolates the foot-target hybrid from the anchor-target hybrid, and the isolated foot-target hybrid is a weak hybrid that makes copying the intended target DNA sequence unlikely as evidenced by a delay of at least two, preferably at least five, cycles in the threshold value (Ct) as compared to the Ct that would occur using a conventional primer that is free of any bridge DNA sequence;

(iii) the probability that during PCR amplification the multi-part primer will initiate copying of any closely related mutant target DNA sequence or the related wild-type target DNA sequence is at least 1,000 times lower than the probability of initiating copying of its intended target sequence, as evidenced by a difference in threshold values (ΔCt) of at least ten thermal cycles;

(iv) the multi-part primer that has generated an amplicon strand has bridge and foot sequences that are perfectly complementary to the amplicon strand's complementary strand; and (v) the length and sequence of the bridge sequence of each multi-part primer, together with the length of the intervening sequence of its intended target sequence, result in a threshold value (Ct) observed for a sample containing only ten copies of its intended target DNA sequence that will occur within 40-65, or preferably 55, cycles of exponential amplification and will be at least two cycles less than the Ct observed from a sample containing no copies.

An allele-discriminating "hairpin" primer is a stem-loop oligonucleotide that, like a molecular beacon probe, contains a single-stranded region (the "loop") flanked by complementary sequences ("arms") that hybridize to one another to form a double-stranded region ("stem"). The loop and the 3' arm of a hairpin primer are sufficiently complementary to the intended target sequence to hybridize thereto under primer-annealing conditions and to initiate copying. An allele-discriminating hairpin primer contains an interrogating nucleotide at or near the middle of the loop sequence.

An ARMS primer is a conventional primer that is allele-discriminating, because its 3'-terminal nucleotide is an interrogating nucleotide. An ARMS primer may include a deliberately introduced nucleotide near its 3' end that is mismatched both to the intended target sequence and to the unintended target sequence to destabilize the primer and increase its allele discrimination.

A "conventional" primer is a single-stranded oligonucleotide that is 15-40 nucleotides in length, more usually 20-30 nucleotides in length, and that is perfectly complementary to the intended target. Any of several computer programs are commonly used to design conventional PCR primers.

Our convention for describing a primer pair is to refer to the limiting primer as the "forward" primer that is complementary to the (−) template strand of the target, and to refer to the excess primer as the "reverse" primer that is complementary to the (+) template strand of the target. We do that for convenience only. It will be understood that the limiting primer may be complementary to the (+) strand, and the excess primer may be complementary to the (−) strand.

Our nomenclature for primers is illustrated by the limiting SuperSelective primer in Example 1, whose sequence is:

(SEQ ID NO: 1)

5'-ACCTGCCGTCAACACGTGCGCAGTAGACCATC-TCTCTTGAGGATC TTGAAGGAAACTGAA-CCTCTCCAACGAATCTCGAA-AAGTGCTGT-3'

In the 5' to 3' direction, this primer contains four elements, separated by dashes (−). In our nomenclature, this primer is 32-28-20/13-8:1:0. The element 32 indicates a 5'-tag sequence that is 32-nucleotides long; the next element, 28, indicates an anchor sequence that is 28-nucleotides long; the next element, 20/13, indicates a bridge sequence 20-nucleotides long that is opposite an intervening sequence in the target sequence of 13 nucleotides; and the final element, 8:1:0, indicates a foot sequence that is nine-nucleotides long (8+1+0), and that has 8 nucleotides from the 5' end that are complementary both to the intended target sequence and to the closely related unintended target sequence, one interrogating nucleotide that is complementary to the intended target sequence but mismatched to the unintended target sequence, and zero nucleotides 3' from the interrogating nucleotide that are complementary to both the intended and unintended target sequences (that is, the interrogating nucleotide in this primer is the 3' terminal nucleotide). If the foot had contained a destabilizing nucleotide, as often occurs in an ARMS primer, it would be italicized in the sequence and represented by an "m" in the characterization. For example, a foot sequence AAGTGCCGT-3' is written 6:m1:1:1:0, indicating that it has 6 nucleotides from the 5' end that are target-complementary; followed by one nucleotide, indicated by an "m", that is mismatched to both the intended and unintended target sequences; followed by one nucleotide that is target-complementary; followed by the interrogating nucleotide; and finally followed by the number of 3' nucleotides (here 0) that are target-complementary. Because the bridge sequence is characterized, not only by its length but by the length of the opposed intervening sequence, the size of the circumference of the bubble is ascertainable as the length of the bridge sequence plus the length of the intervening sequence plus 4, as the bubble includes a hybridized base pair on each side. In the sequence example above, the circumference of the bubble is 37 nucleotides (20+13+4=37).

DETAILED DESCRIPTION

Shown in FIG. 1 is an embodiment of a method of this invention of the first type, wherein the first primer is an allele-discriminating multi-part primer and the second primer is an allele-discriminating primer, both of which are complementary to a single base-pair mutation (a SNP) in a rare mutant target sequence. In the top panel the primers are shown hybridized to (indicated by short vertical lines) a rare target sequence in a double-stranded template containing a plus (+) strand and a minus (−) strand. Although only one primer must be a multi-part primer, preferably a SuperSelective primer, the depicted embodiment has a pair of SuperSelective primers. As shown in the top sketch, each primer has an anchor sequence, an unhybridized bridge sequence opposite an intervening sequence in the template, and a foot sequence. The intended target sequence (for purposes of illustration said to be the EGFR gene, as in Example 1) contains a single base pair that differs from a closely related sequence. For the purpose of illustration, that base pair is designated as an A nucleotide in the (−) template strand of the intended target sequence and a T nucleotide in the (+) template strand of the intended target sequence. That is, the mutation to be detected is a single-nucleotide polymorphism that occurs in Exon 18 of the EGFR gene (EGFR G719C), which is the subject of Example 1. Each primer has an interrogating nucleotide, here a 3'-terminal interrogating nucleotide, that is complementary to one nucleotide of that base pair. FIG. 1 depicts an embodiment in which the amplification reaction is non-symmetric. One primer, here designated as the forward primer, which is also the limiting primer as indicated in the middle panel, contains a 5'-tag sequence that is not complementary to the target strand but is copied in the amplification reaction. The other primer, here designated as the reverse primer, is also the excess primer as indicated in the middle panel. Also shown in the top sketch is a homogeneous fluorescence detection probe, here a hairpin-shaped molecular beacon probe having a single-stranded loop and a double-stranded stem, wherein one arm of the stem is labeled with a fluorophore (○) and the other arm of the stem is labeled with a quencher (●). In the embodiment depicted, the molecular beacon is a "conventional" molecular beacon probe, that is, a molecular beacon probe in which only its single-stranded loop is made complementary to the probe's target, which in this case is the complement of the 5'-tag sequence. The bottom sketch shows detection, which can be real-time detection or end-point detection as is used in digital PCR methods. The probe is shown hybridized to the (−) amplicon, that is, the amplification product produced by extension of the excess primer, the probe's target being the complement of the limiting primer's 5'-tag sequence. The probe's fluorophore is separated from the probe's quencher by hybridization of the probe to its target, and consequently fluoresces (Tyagi et al. (1998) Nature Biotechnology 16:49-53).

Figure 3:
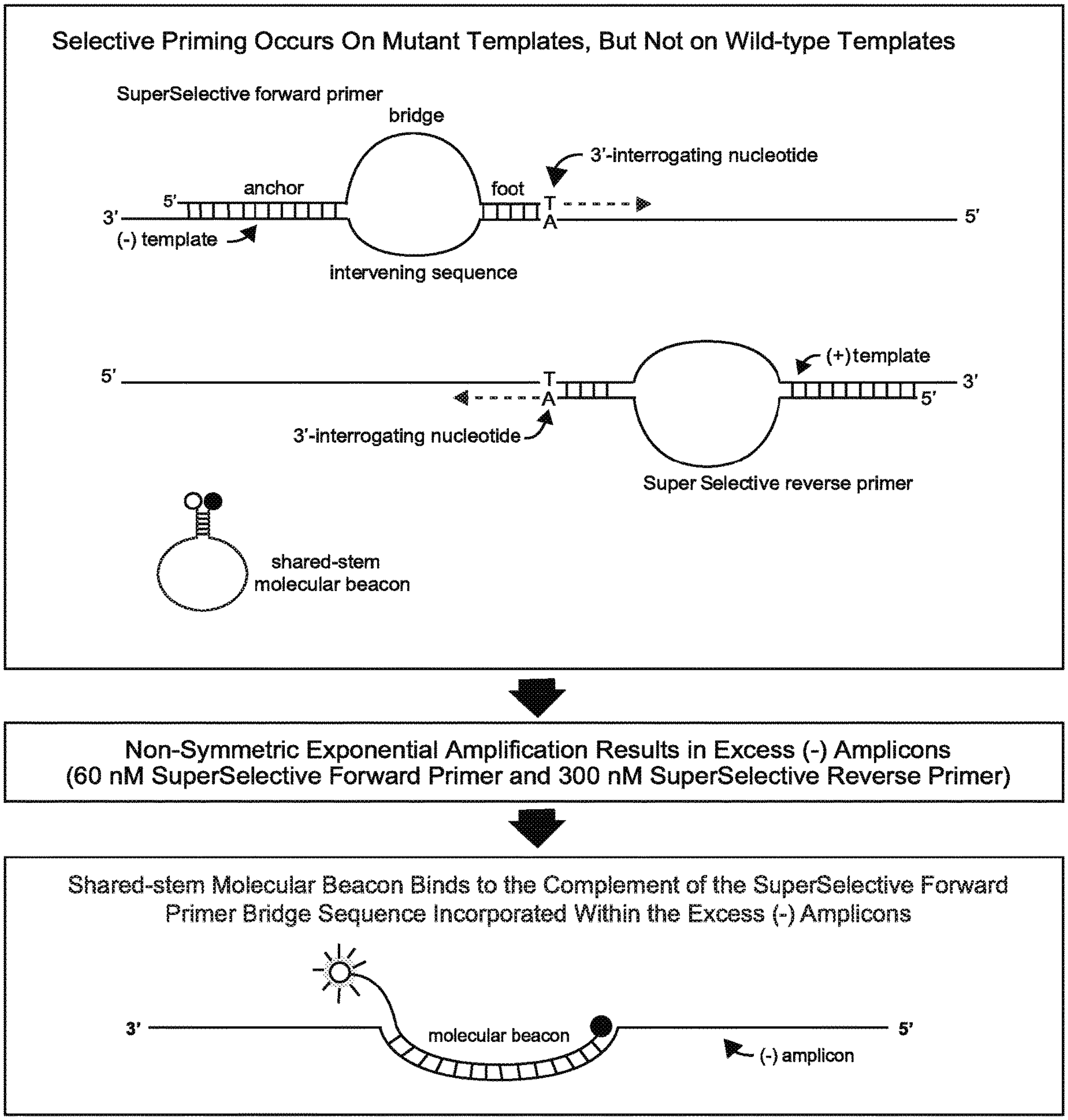
FIG. 3 depicts the design of the method of Example 2 for detecting rare copies of a mutation utilizing a pair of SuperSelective primers complementary to the mutation, with detection by a shared-stem molecular beacon probe targeting the complement of the bridge sequence of the limiting SuperSelective forward primer.

Shown in FIG. 3 is an embodiment similar to that shown in FIG. 1, except that the target of the probe is the complement of the limiting primer's bridge sequence, rather than the complement of the limiting primer's 5'-tag sequence, and so the limiting primer does not contain a 5'-tag sequence. In the embodiment depicted, the molecular beacon probe, sometimes referred to as a "shared-stem" molecular beacon (Tsourkas et al. (2002) Nucleic Acids Research 30:4208-4215), has one arm, in this case the arm labeled with a quencher, that is also complementary to the probe's target. Thus, as shown in the bottom sketch, both the loop and that arm hybridize to the complement of the limiting primer's bridge. For the purpose of illustration that base pair that occurs in the rare target, but not in a closely related sequence, is designated as an A nucleotide in the (−) strand of the intended target sequence and a T nucleotide in the (+) strand of the intended target sequence. That is, the mutation to be detected is a single-nucleotide polymorphism that occurs in Exon 20 of the EGFR gene (EGFR T790M), which is the subject of Example 2.

In FIGS. 1 and 3, one detection probe is shown to hybridize to one sequence that is the target of the probe. That does not preclude the inclusion of two sequences that are probe targets. For example, if the complement of the bridge sequence of one primer is the target of a first probe, the complement of a 5'-tag sequence of the other primer could be a target for a different probe of the same color, in which case twice as many probe copies could bind and fluoresce.

Example 1 illustrates the embodiment of the method according to this invention that is depicted in FIG. 1. The rare intended target sequence is mutation G719C in the EGFR gene. Detection of this mutation enables a particularly effective targeted therapy (Erlotinib or Gefitinib) to be used to kill cancer cells containing that mutation that are present in a patient's non-small cell lung cancer (Pao et al. (2004) Proceedings of the National Academy of Sciences of the United States of America 101:13306-13311; Kobayashi and Hagiwara (2013) Targeted Oncology 8:27-33).

A multi-part first primer, here a SuperSelective limiting primer, and an allele-discriminating second primer, here also a SuperSelective primer, both interrogated a single base pair. The rare intended target sequence, in this case mutation G719C in the EGFR gene, differed from the abundant closely related unintended target sequence, in this case the wild-type sequence, by a single base-pair change. In this case A:T in the mutant (see FIG. 1) differed from C:G in the wild type. The amplification and detection method was a real-time PCR assay. For comparison, in Example 1, the excess SuperSelective primer (for convenience referred to as the reverse primer) was replaced with a conventional PCR reverse primer (in this case the sequence of the SuperSelective reverse primer's anchor sequence) that was complementary to both the intended and unintended target sequences.

In Example 1, the foot sequence of the SuperSelective forward primer was nine-nucleotides long, and the circumference of the bubble formed when the primer hybridized to the intended target sequence was 37 nucleotides (20+13+4). The foot sequence of the reverse primer was also nine-nucleotides long, and the circumference of the bubble formed when that primer hybridized to the intended target sequence was 32-nucleotides long (18+10+4). We have found that methods according to this invention that employ SuperSelective primers that have relatively long (8-12 nucleotides) feet with no destabilizing nucleotides and that create relatively large bubble circumferences (28-50 nucleotides), benefit from inclusion of a selectivity-enhancing reagent. In Example 1, 50 mM tetramethylammonium chloride was included in each amplification reaction mixture as an effective amount of selectivity-enhancing reagent.

Samples were subjected to PCR amplification with real-time fluorescence detection. One sample contained only 10,000 copies of the EGFR wild-type sequence. A second sample contained ten copies of the G719C mutant sequence in a mixture containing 10,000 copies of the EGFR wild-type sequence. A third sample contained 100 copies of the G719C mutant sequence in a mixture containing 10,000 copies of the EGFR wild-type sequence. Each sample was tested in duplicate reactions. Fluorescence intensity curves from the amplification reactions are presented in FIG. 2. For each primer pair, the average Ct values (of the two replicates) for the sample containing only wild-type and for the sample containing ten copies of the mutant are set forth in Table 1, as is the ΔCt. Comparing the method using two SuperSelective primers that both select against a single SNP (bottom panel B of FIG. 2) with a method utilizing the same limiting SuperSelective forward primer and a conventional reverse primer (top panel A of FIG. 2), one sees that, while the latter can indeed distinguish ten mutants in 10,000 wild types from 10,000 wild types, the method of this invention does so much more robustly. Table 1 shows that whereas the ΔCt for the primer pair that included a conventional primer was 2.95, the ΔCt for the primer pair that included two SuperSelective primers was 12.87. That was an increase of nearly 10 cycles, evidencing that the method of Example 1 utilizing a pair of SuperSelective primers is a method according to this invention.

Example 2 illustrates the embodiment of the method according to this invention that is depicted in FIG. 3. The target-sequence mutation was T790M, which is located in Exon 20 of the EGFR gene. The mutation is a single base-pair substitution (SNP) of an A:T base pair in place of the G:C base pair that occurs in the otherwise identical closely related wild-type sequence. Detection of this mutation indicates that the commonly utilized targeted therapy (Erlotinib or Gefitinib), which kills cancer cells that contain any one of a number of different EGFR mutations (including G719C, G719S, L858R, L861Q, and E746-A750 deletions), will not work, but a different targeted therapy (Osimertinib) is likely to kill those cancer cells in a patient's non-small cell lung cancer (Lamb and Scott (2017) Targeted Oncology 12:555-562).

The amplification and detection method was a real-time PCR method similar to the method of Example 1, except that the target mutation was EGFR mutation T790M, and the homogeneous detection probe was a shared-stem molecular beacon targeting the complement of the bridge sequence of the SuperSelective forward primer, which did not include a 5'-tag sequence. In this case, A:T in the mutant (see FIG. 3) differed from G:C in the wild type. As in Example 1, one set of reactions utilized a pair of SuperSelective primers, each having an interrogating 3'-terminal nucleotide, and a second set of reactions utilized the limiting SuperSelective forward primer and a conventional reverse primer that was complementary to both the intended and unintended target sequences, in this case having the sequence of the anchor sequence of the SuperSelective reverse primer. Both pairs of primers were tested against three samples. The samples contained 10,000 copies of the wild-type's closely related unintended target sequence plus 0, 10 or 100 copies of the mutant's intended target sequence. 50 mM TMAC was included in each amplification reaction mixture as an effective amount of selectivity-enhancing reagent.

Figure 4:
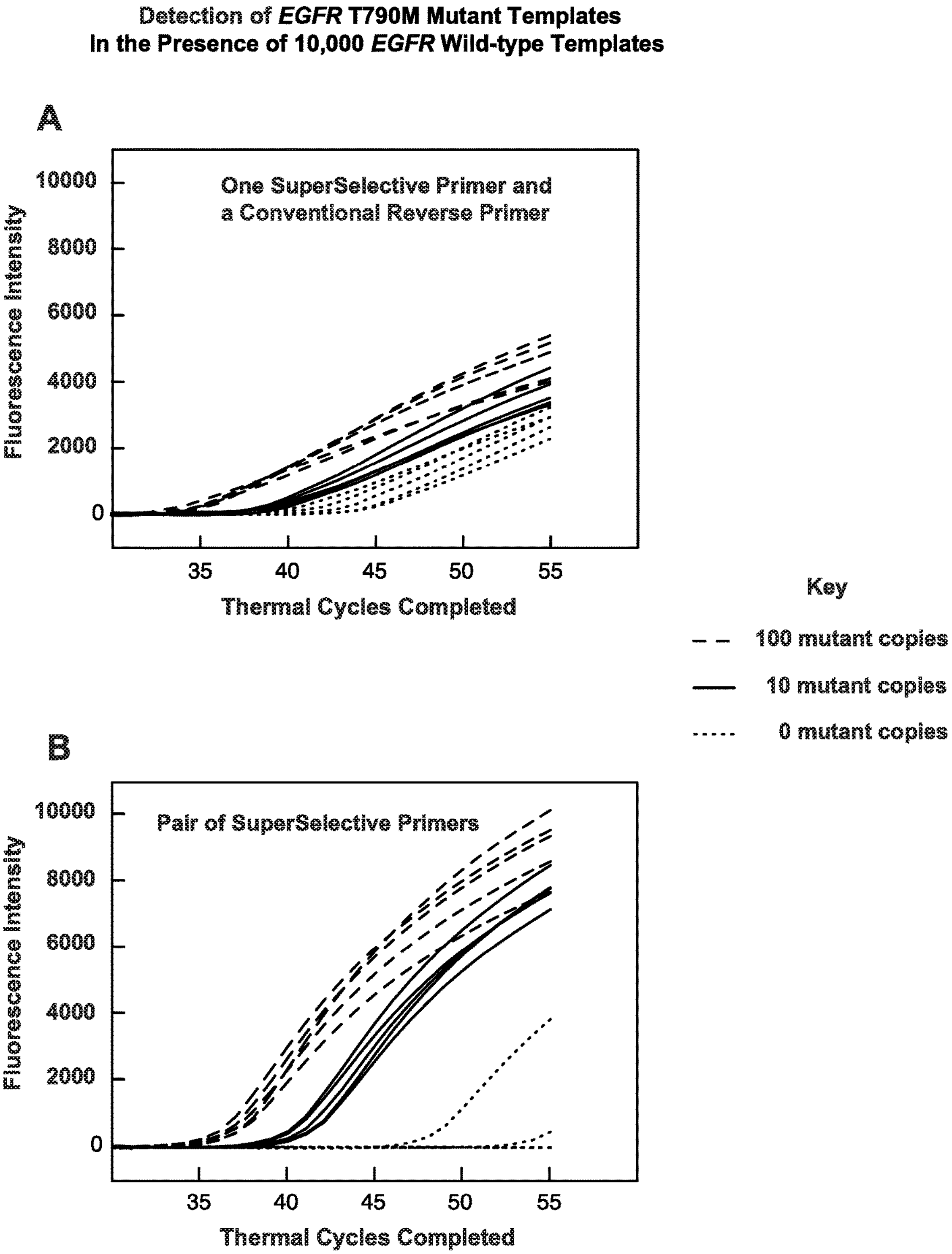
FIGS. 4A and 4B show the results of the real-time PCR assays of Example 2, wherein top panel A shows amplification and detection utilizing a SuperSelective forward primer complementary to the EGFR T790M mutation and a conventional reverse primer complementary to both the mutant sequence and to its closely related wild-type sequence downstream from the target mutation; and bottom B panel shows the results of an otherwise identical real-time PCR assay that utilizes a pair of SuperSelective primers, both of whose 3'-interrogating nucleotides are complementary to the T790M target mutation.

Five replicates of each sample were subjected to PCR amplification with real-time fluorescence detection. Fluorescence intensity curves from the amplification reactions are presented in FIG. 4. For each primer pair, the average Ct values (of the five replicates) for the samples containing only wild-type and for the samples containing ten copies of the mutant in the presence of 10,000 wild types are set forth in Table 2, as is the ΔCt between those average Ct values. Table 2 shows that the method utilizing the SuperSelective forward limiting primer and a conventional reverse primer gave a substantial average ΔCt of 5.35. However, top panel A of FIG. 4 shows that, due to variability among replicates, several replicates are needed to achieve that result. In contrast, the method using two SuperSelective primers did so much more robustly. Bottom panel B of FIG. 4 shows that fluorescence from the wild-type-only sample was significantly delayed, and three of the five replicates gave no Ct through 55 cycles. To calculate and average Ct, those replicates are assigned a Ct of >55. Doing that, the average ΔCt was >14.00. That was an increase of nearly 9 cycles, evidencing that the method of Example 2, utilizing a pair of SuperSelective primers, is a method according to this invention.

Figure 5:
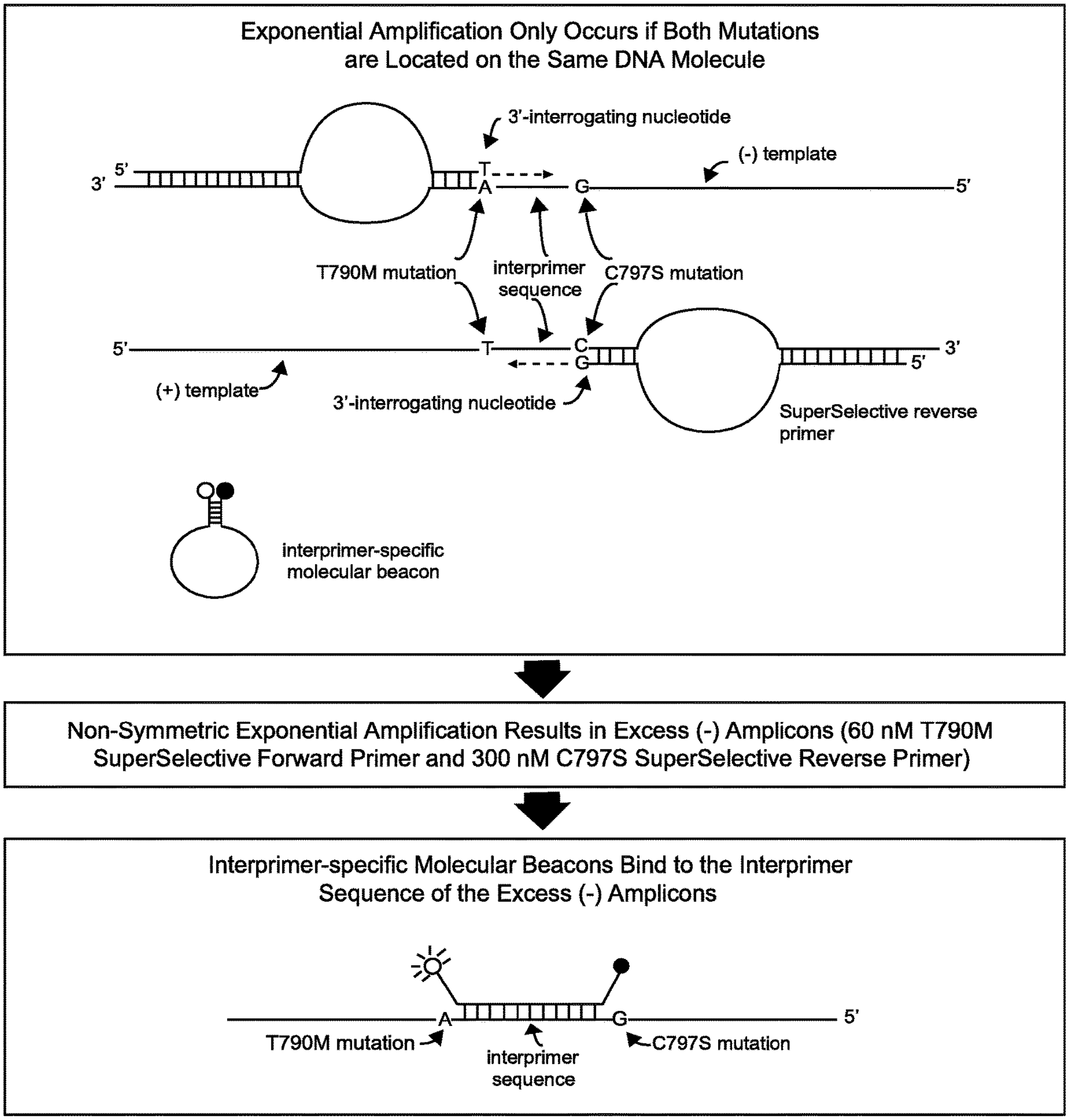
FIG. 5 depicts the design of the method of Example 3 for determining whether two mutations occur on the same chromosome (in cis) using a SuperSelective forward primer complementary to one mutation and a SuperSelective reverse primer complementary to the other mutation.

Shown in FIG. 5 is an embodiment of this invention having a pair of multi-part primers hybridized to (indicated by short vertical lines) a rare target sequence in a double-stranded template containing a plus (+) strand and a minus (−) strand. Although only one primer must be a multi-part primer, the depicted embodiment has a pair of SuperSelective primers. As shown in the top sketch, each primer has an anchor sequence, an unhybridized bridge sequence opposite an intervening sequence in the template, and a foot sequence. The intended target sequence contains two mutant base pairs that differ from a closely related sequence. For the purpose of illustration, the first mutant base pair is designated as an A nucleotide in the (−) template strand of the intended target and a T nucleotide in the (+) template strand of the intended target. That is, the first mutation to be detected is a single-nucleotide polymorphism that occurs in Exon 20 of the EGFR gene (EGFR T790M). The second mutant base pair is designated as a G in the (−) template strand of the intended target and a C in the (+) template strand of the intended target. That is, the second mutation to be detected is a single-nucleotide polymorphism that also occurs in Exon 20 of the EGFR gene (EGFR C797S).

In the embodiment of this invention depicted in FIG. 5, the object is to identify the presence in a sample of chromosomes that contain both of the target mutations (in this case, the presence of both EGFR T790M and EGFR C797S). The occurrence of the two target mutations on the same chromosome (i.e., in cis) in a sample, as described in Example 3, is differentiated, not only from a sample having only closely related wild-type sequences, but also from a sample containing the same two mutations, but each located on a different sister chromosome (i.e., in trans). Each primer has an interrogating nucleotide, here a 3'-terminal interrogating nucleotide, that is complementary to one of the two mutations. One primer, here designated the forward primer, which is also the limiting primer as indicated in the middle panel, has its interrogating nucleotide complementary to the T790M mutation in the (−) template strand. The other primer, here designated the reverse primer, which is the excess primer as indicated in the middle panel, has its interrogating nucleotide complementary to the C797S mutation in the (+) template strand. Also shown in the top sketch is a homogeneous fluorescent detection probe, here a molecular beacon probe, having a single-stranded loop and a double-stranded stem, wherein one arm of the stem is labeled with a fluorophore (○) and the other arm is labeled with a quencher (●). In the embodiment depicted, the molecular beacon is a "conventional" molecular beacon probe, that is, a molecular beacon probe in which only its single-stranded loop is made complementary to the probe's target, which in this case is the complement of the region between the primer sequences in the amplified product. The bottom sketch shows detection, which can be either real-time detection or end-point detection as is used in digital PCR methods. This "interprimer-specific" probe is shown hybridized to the (−) amplicon with the probe's fluorophore separated from the probe's quencher by hybridization of the probe.

Example 3 illustrates the embodiment of the method according to this invention that is depicted in FIG. 5. Two different target mutations, T790M (which has an A:T base pair in place of a G:C base pair in Exon 20 of the EGFR gene) and C797S (which has a G:C base pair in place of a C:G base pair in the same exon) are located 20 nucleotides apart from each other if they occur on the same chromosome, that is, if they occur in cis. The purpose of the assay shown in Example 3 is to determine whether or not these two mutations (if they are both present in the sample) do indeed occur on the same chromosome, or whether (if they are both present) they occur on sister chromosomes, that is, whether they occur in trans. If only one of these two somatic mutations occurs in a sample from a patient who has non-small cell lung cancer, or if both occur but in trans on sister chromosomes (Vokes and Jänne (2017) Journal of Thoracic Oncology 12:1608-1610), Osimertinib will be an effective targeted therapy (Lamb and Scott (2017) Targeted Oncology 12:555-562). However, if both of these mutations occur in cis on the same chromosome, then there will be two amino acid substitutions in the resulting EGFR protein, and Osimertinib will not be an effective targeted therapy (Wang et al. (2016) Journal of Hematology and Oncology 9:59). Instead, Brigatinib will be effective in its place (Uchibori et al. (2017) Nature Communications 8:14768).

Figure 6:
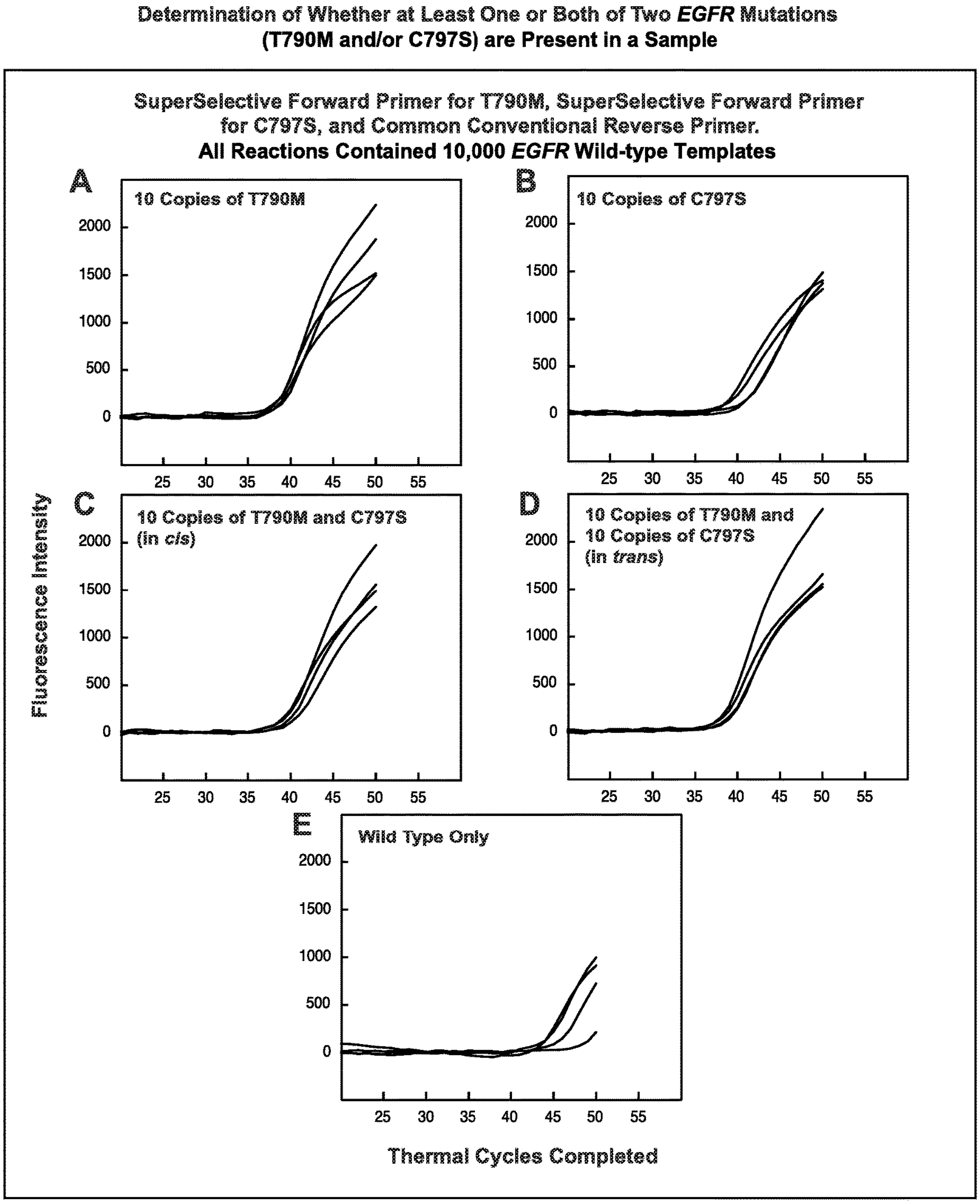
FIGS. 6A, 6B, 6C, 6D, and 6E show the results of the real-time PCR assays of Example 3, wherein the reaction mixtures contain a SuperSelective forward primer for the EGFR T790M mutation, a SuperSelective forward primer for the EGFR C797S mutation, and a conventional reverse primer. (A) 10 copies of T790M, (B) 10 copies of C797S, (C) 10 copies of T790M and of C797S (in cis), (D) 10 copies of T790M and 10 copies of C797S (in trans), and (E) wild type only.

To obtain a reference for assessing ΔCt and to illustrate why the method is necessary, a first series of amplifications was performed utilizing a conventional primer as the reverse primer, with real-time fluorescence curves reported in FIG. 6. Bottom panel E presents fluorescence curves for four replicates of a sample containing only 10,000 copies of the closely related (wild-type) EGFR sequence; top left-hand panel A presents curves for four replicates of a sample containing 10,000 copies of the EGFR wild-type sequence plus ten copies of the EGFR T790M sequence; top right-hand panel B presents curves for four replicates of a sample containing 10,000 copies of the EGFR wild-type sequence plus ten copies of the EGFR C797S sequence; middle right-hand panel D presents curves for four replicates of a sample containing 10,000 copies of the EGFR wild-type sequence plus ten copies of the EGFR T790M sequence and ten copies of the EGFR C797S sequence (i.e., the two mutations are present in trans); and middle left-hand panel C presents curves for four replicates of a sample containing 10,000 copies of the EGFR wild-type sequence plus ten copies of a sequence containing both the EGFR T790M mutation and the EGFR C797S mutation (i.e., the two mutations are present in cis). As shown in Table 3, the average Ct value for the samples containing only 10,000 wild-type templates was 45.82, whereas the average Ct values for the four different types of samples containing 10 copies of one or both mutant templates in addition to 10,000 wild-type templates were 38.34, 39.95, 38.44, and 39.49 (which aggregately had an average Ct value of 39.05). The key point here is that although the presence of one or both mutations in a sample was indicated by an average Ct value that was lower than the Ct value of a sample containing only wild-type templates (average ΔCt of 6.77), the trans configuration, whose replicate curves are shown in middle right-hand panel D, had an average Ct value of 38.44, which was nearly identical to the cis configuration, whose replicate curves are shown in middle left-hand panel C, and which gave a very similar average Ct value of 39.49. Thus, the cis configuration could not be distinguished from the trans configuration.

Figure 7:
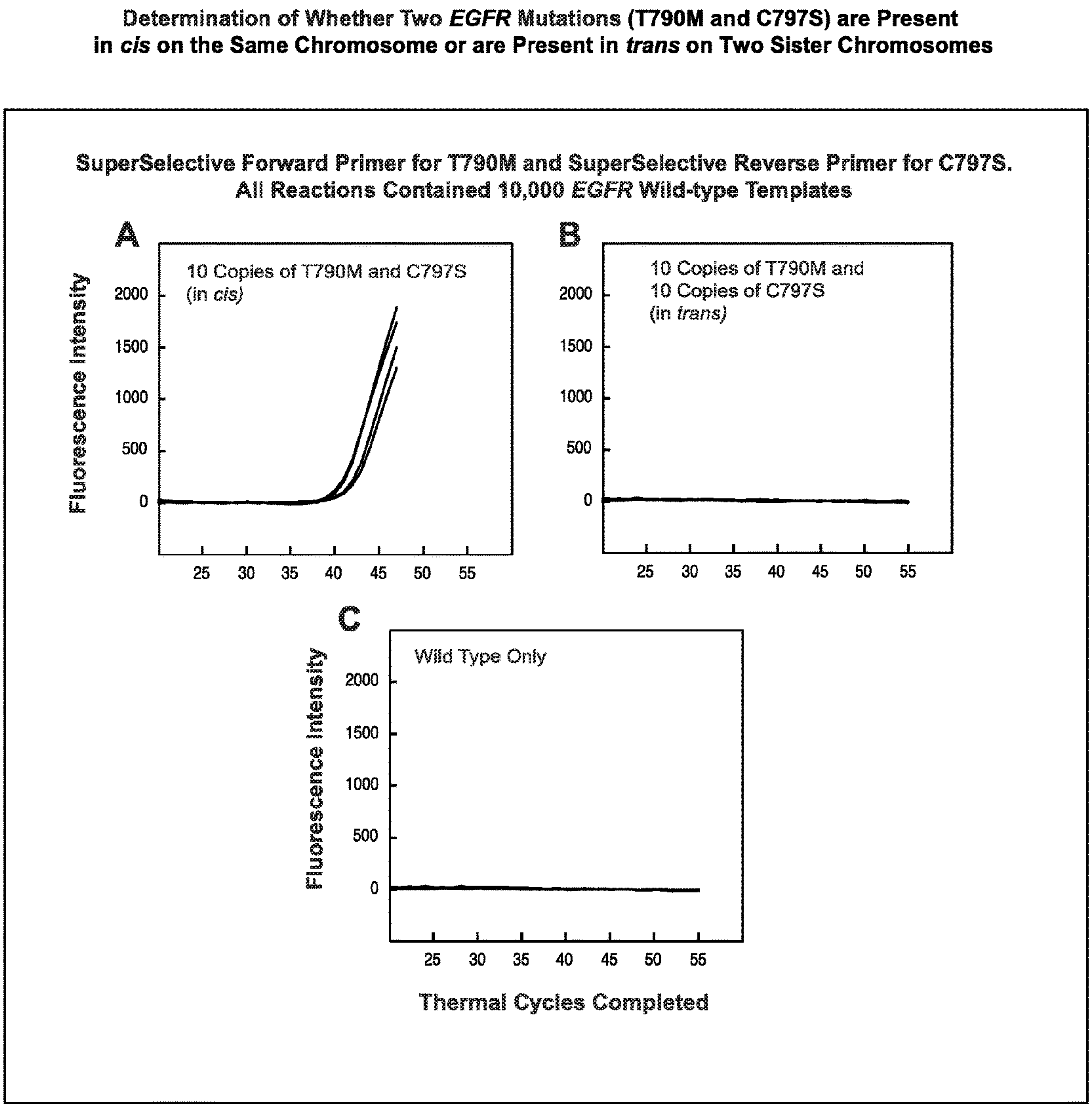
FIGS. 7A, 7B, and 7C show the results of the real-time PCR assays of Example 3, wherein the reaction mixtures contain a SuperSelective forward primer complementary to one mutation, and a SuperSelective reverse primer complementary to the other mutation. (A) 10 copies of T790M and of C797S (in cis), (B) 10 copies of T790M and 10 copies of C797S (in trans), and (C) wild type only.

To make that distinction, a second series of amplifications was performed utilizing the method shown in FIG. 5. Real-time PCR amplification and detection were performed with samples containing either both mutations in the cis configuration, or with samples containing both mutations in the trans configuration, utilizing a pair of SuperSelective primers, as depicted in FIG. 5, with real-time fluorescence curves reported in FIG. 7. Bottom panel C presents fluorescence curves for four replicates of a sample containing only 10,000 copies of the wild-type sequence; upper left-hand panel B presents curves of four replicates of a sample containing 10,000 copies of the wild-type sequence plus 10 copies of the two mutations in cis configuration; and upper right-hand panel B presents curves of four replicates of a sample containing 10,000 copies of the wild-type sequence plus 10 copies of the two mutations in separate sequences, that is, in trans configuration. The average Ct value for the cis sample was 41.31. Neither the trans sample nor the wild-type-only sample exhibited fluorescence above background through 55 amplification cycles. Assigning each a Ct value of >55, as we prescribe, the ΔCt value was 13.69. This method qualifies as a method according to this invention. It meets the criterion that neither sample with no cis templates (the intended target sequence) produced a Ct value above background within 55 cycles of amplification. Further, because the ΔCt value relative to the wild-type-only sample increased by 13.69 cycles, it meets the alternative criterion of an increase of at least 5 cycles.

Figure 8:
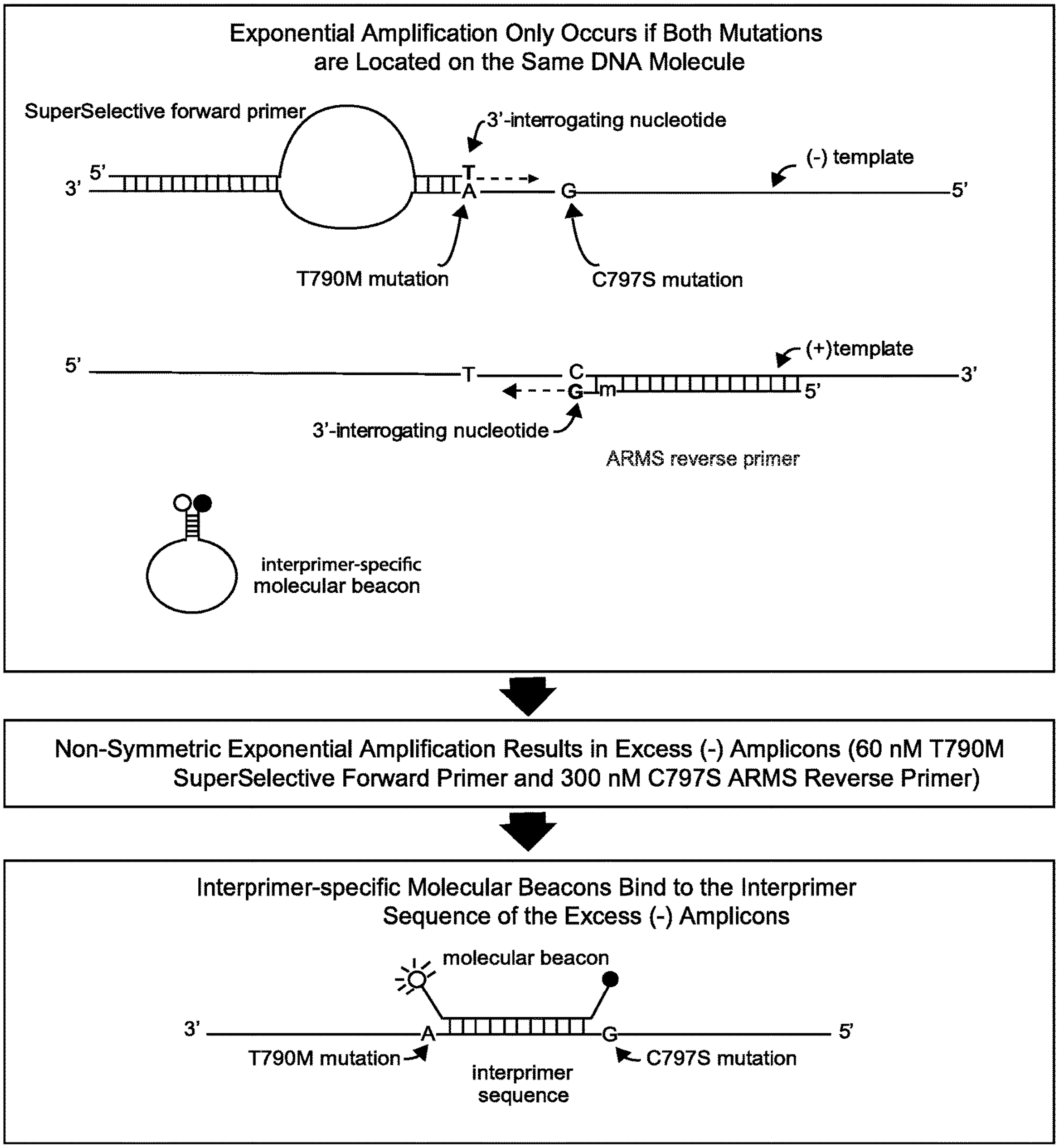
FIG. 8 depicts the design of the method of Example 4 for determining whether two mutations occur on the same chromosome (in cis) using a SuperSelective forward primer complementary to one mutation and an ARMS reverse primer complementary to the other mutation.

In Example 4, the method of the second series of amplifications in Example 3 was repeated substituting an ARMS primer as the reverse primer in place of the SuperSelective reverse primer. The method for detecting two mutations in cis configuration is depicted in FIG. 8, and real-time fluorescence curves are reported in FIG. 9, where bottom panel C presents fluorescence curves for four replicates of a sample containing only 10,000 copies of the wild-type sequence; upper left-hand panel A presents curves of four replicates of a sample containing 10,000 copies of the wild-type sequence plus 10 copies of the two mutations in cis configuration; and upper right-hand panel B presents curves of four replicates of a sample containing 10,000 copies of the wild-type sequence plus 10 copies of the two mutations in separate sequences, that is, in trans configuration. The average Ct value for the cis sample was 43.31. Neither the trans sample nor the wild-type-only sample exhibited fluorescence above background through 55 amplification cycles. Assigning each a Ct value of >55, as we prescribe, the ΔCt value was 11.69. This method qualifies as a method according to this invention. It meets the criterion that neither sample with no cis templates (the intended target sequence) produced a Ct value above background within 55 cycles of amplification. Further, because the ΔCt value relative to the wild-type-only sample increased by 11.69 cycles, it meets the alternative criterion of an increase of at least 5 cycles.

Example 5 illustrates the use of an ARMS primer as the second primer in a method to detect a single base-pair change. Assays were performed to demonstrate the use of an ARMS primer as either the limiting primer or the excess primer. As described in Example 5, real-time PCR assays with real-time detection were carried out to detect 10 copies of a rare KRAS G12D intended mutant target sequence in a mixture containing 10,000 copies of its closely related unintended wild-type target sequence, utilizing several different primer pairs: a limiting ARMS forward primer with an excess SuperSelective reverse primer, a limiting SuperSelective forward primer with an excess ARMS reverse primer, and a pair of SuperSelective primers (as a control). Each multi-part primer and each ARMS primer had a 3'-terminal interrogating nucleotide that was complementary to a nucleotide of the mutant base pair.

Figure 11:
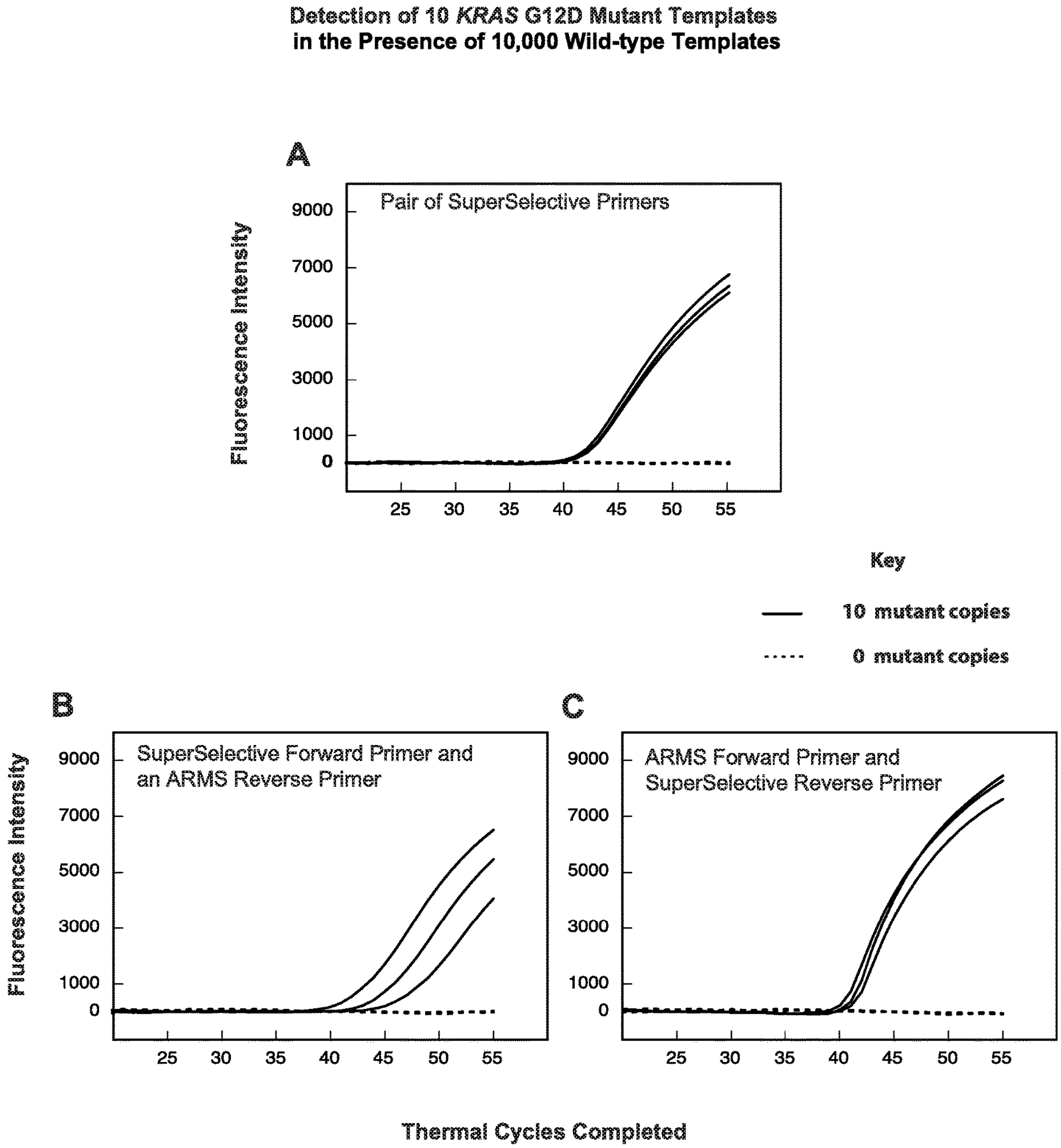

The method in which the ARMS primer was the forward primer is depicted in FIG. 10. The results of these assays are shown in FIG. 11. For all primer pairs containing a SuperSelective primer as the multi-part first primer, the fluorescence intensity of samples containing only unintended (wild-type) template sequences did not rise above background through 55 amplification cycles. Therefore, the method utilizing each of those primer pairs is a method according to this invention.

Example 6 illustrates the selectivity and sensitivity of real-time PCR assays that are designed to detect the presence of, and determine the relative abundance of, rare mutant target DNA fragments in a sample containing abundant DNA fragments from the entire normal human genome. In particular, this example demonstrates that the use of a pair of allele-discriminating multi-part primers, both of which are complementary to a single base-pair mutation present in rare DNA fragments, that are analyzed in real-time PCR assays in which the sample includes abundant DNA fragments from the entire normal human genome, enables the reliable detection of a very small number of target fragments. In particular, every one of ten samples that each nominally contained 5 mutant DNA fragments in the presence DNA fragments from 10,000 copies of the entire normal human genome gave a positive signal for the presence of the mutant DNA fragments. As a control, all ten samples that contained no mutant DNA fragments, but did contain DNA fragments from 10,000 copies of the entire normal human genome, did not give a positive signal for the presence of the mutant DNA fragments.

These results imply that positive results in assays employing pairs of allele-discriminating primers, such as SuperSelective primers, both of which are specific for the same mutant base pair, can be relied on to indicate a true-positive result; and negative results in these same assays can be relied on to indicate a true-negative result. This is a key criterion for extremely sensitive PCR assays, such as assays designed to detect the presence of rare mutant fragments in cell-free DNA isolated from the plasma of a 10 mL blood sample obtained from a patient with cancer, where the presence of particular mutations indicates that particular targeted therapies will be effective (Sabari et al. (2019) Journal of the National Cancer Institute 111:575-583).

All of the assays carried out in this example contained DNA fragments from 10,000 copies of the entire normal human genome. This is greater than the amount of cell-free DNA fragments usually isolated from 1 mL of plasma obtained from a patient's 10 mL blood sample (Meddeb et al. (2019) Scientific Reports 9:5220). However, since the actual amount of cell-free DNA fragments in a patient's blood sample can vary from hour to hour, it is important to include in real-time PCR assays primers and probes that detect DNA fragments from a normal reference gene, thereby enabling the amount of DNA in the sample to be determined. The results will then indicate whether there is enough DNA in the sample to be able to detect rare mutant DNA fragments. Moreover, the threshold cycle (Ct) obtained in a PCR assay for the mutant target fragment compared to the threshold cycle obtained for the reference gene (ΔCt) enables the results to be expressed as the relative abundance of that mutation in the patient's DNA, which is the clinically relevant result.

Figure 12:
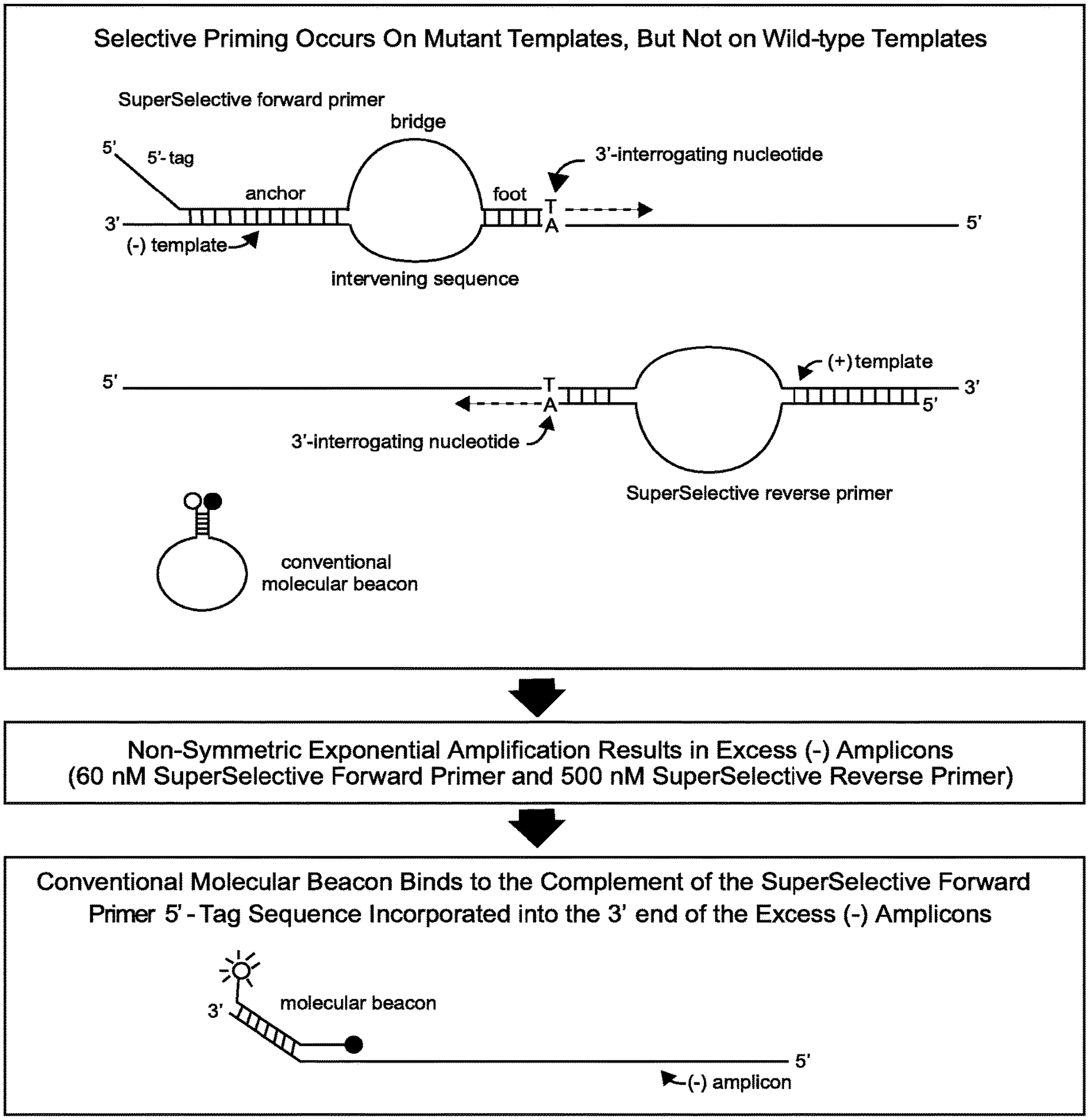
FIG. 12 depicts the design of the method of Example 6 for detecting rare copies of a mutation in the presence of abundant copies of normal human genomic DNA, utilizing a pair of SuperSelective primers complementary to the mutation, where detection is accomplished with a conventional molecular beacon probe labeled in one fluorescent color targeting the complement of the 5'-tag on the limiting SuperSelective primer; and where these assays also included a SuperSelective primer and a conventional reverse primer for the β-actin reference gene in normal human genomic DNA, where detection of that reference gene is simultaneously accomplished with an interprimer-specific molecular beacon labeled in a different fluorescent color, thereby enabling the relative abundance of the rare mutation to be assessed by comparison of the difference in the threshold values of the mutant and the reference gene.

FIG. 12 illustrates how a pair of SuperSelective primers for the G719C mutation in the EGFR gene was utilized in the assays of Example 6. The limiting primer for the G719C gene contained a 5'-tag sequence, and a FAM-labeled conventional molecular beacon present in the assays signals the presence of amplicons generated as result of the presence of mutant DNA fragments in the sample by binding to the complement of the 5'-tag sequence that is incorporated into the 3' end of the excess (−) amplicons. All of the assays carried out in Example 6 also contained a limiting concentration of a SuperSelective forward primer for the human β-actin gene, an excess concentration of a conventional reverse primer for the β-actin gene, and a Quasar 705-labeled interprimer-specific molecular beacon that signals the presence of amplicons generated from the β-actin reference gene.

Four sets of ten assays were carried out, in which every assay contained 10,000 copies of DNA restriction fragments from normal human genomic DNA. In addition, in every assay, the first set also contained 500 copies of a linearized plasmid containing the mutant target sequence, the second set also contained 50 copies of mutant DNA plasmids, the third set also contained 5 copies of mutant DNA plasmids, and the fourth set served as a negative control that did not contain any mutant DNA plasmids.

Figure 13:
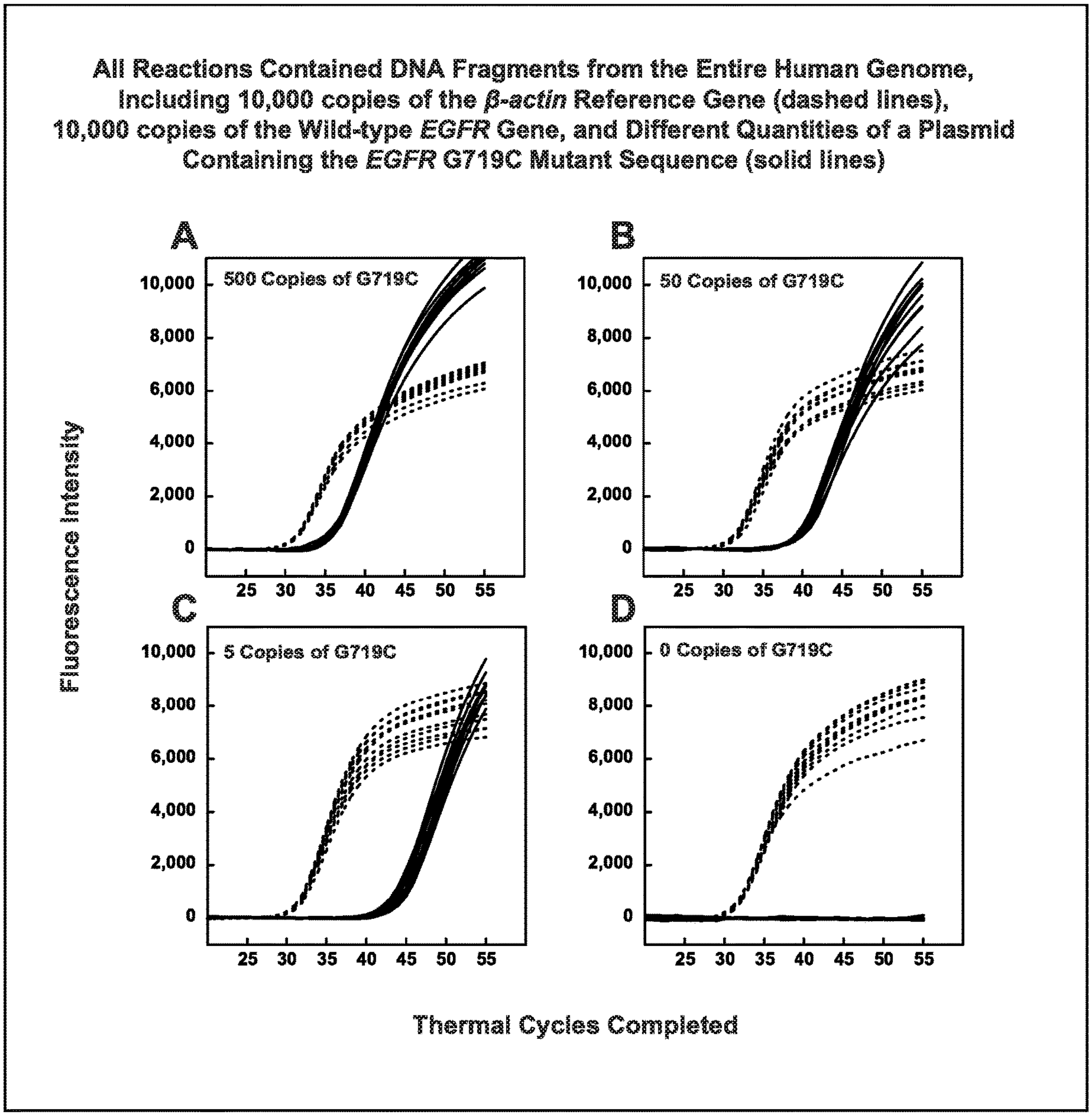
FIGS. 13A, 13B, 13C, and 13D show the results of the real-time PCR assays of Example 6, in which all samples contained the same number of abundant copies of the entire human genome, and each of the four panels shows the results obtained with samples that also contained different quantities of mutant target DNA, including samples that did not contain any mutant target DNA. (A) 500 copies of G719C, (B) 50 copies of G719C, (C) 5 copies of G719C, and (D) 0 copy of G719C.

The results of these 40 PCR assays are shown in FIG. 13. Upper left-hand panel A of FIG. 13 shows the results of assays that each contained 500 mutant plasmids; upper right-hand panel B shows the results of assays that contained 50 mutant plasmids; lower left-hand panel C shows the results of assays that contained only 5 mutant plasmids; and lower right-hand panel D shows the results of assays that did not contain any mutant plasmids.

All of these assays gave a positive FAM signal, and their average Ct value was 43.27. By comparison, all of the reactions that did not contain any mutant plasmids did not produce a FAM signal above background, during the entire 55 cycles of amplification. These results illustrate the extraordinary selectivity and sensitivity of exponential amplification assays employing pairs of allele-specific primers for the detection of single-nucleotide polymorphisms, suggesting that assays utilizing these primer pairs will enable extremely sensitive clinical assays that can be carried out relatively rapidly, at low cost, in widely available instruments.

Compositions and Kits

The invention encompasses a composition or reaction mixture comprising the aforementioned primers and reagents for carrying out the methods described above. For example, the composition can comprise one or more reagents selected from the group consisting of a nucleic acid polymerase, deoxyribonucleoside triphosphates, and a detecting agent.

The detecting agent can be an oligonucleotide probe, such as a molecular beacon probe or a Yin-Yang probe that is labeled with a fluorophore and a quencher. See e.g., U.S. Pat. Nos. 5,925,517, 6,103,476, 6,150,097, 6,270,967, 6,326,145, and 7,799,522. The composition can also comprise, in addition to the above reagents, one or more of: a salt, e.g., NaCl, $MgCl_2$, KCl, $MgSO_4$; a buffering agent, e.g., a Tris buffer, N-(2-Hydroxyethyl)-piperazine-N'-(2-ethanesulfonic acid) (HEPES), 2-(N-Morpholino)ethanesulfonic acid (MES), MES sodium salt, 3-(N-Morpholino)propanesulfonic acid (MOPS), N-tris-[Hydroxymethyl]-methyl-3-amino-pro-panesulfonic acid (TAPS); a solubilizing agent; a detergent, e.g., a non-ionic detergent such as Tween-20; a nuclease inhibitor; and the like.

The reaction components used in an amplification and/or detection process may be provided in a variety of forms. For example, the components (e.g., enzymes, deoxyribonucleoside triphosphates, adaptors, blockers, and/or primers) can be suspended in an aqueous solution or as a freeze-dried or lyophilized powder, pellet, or bead. In the latter case, the components, when reconstituted, form a complete mixture of components for use in an assay.

EXAMPLES

Example 1. Utilization of a Pair of SuperSelective Primers in Real-Time PCR Assays for the Detection of Rare EGFR G719C Mutant Templates in the Presence of Abundant Wild-Type Templates The design of this first example is shown in FIG. 1. The target mutation (G719C), which is located in Exon 18 of the human epidermal growth factor (EGFR) gene, is an A:T base pair in place of the C:G base pair that occurs in the otherwise identical wild-type gene sequence. A PCR assay was carried out utilizing mutant and wild-type plasmids containing the target gene sequence, in which the "anchor" sequence of one SuperSelective primer (which we will call the "forward" primer) binds to all (−) template strands (both the rare intended target and the abundant unintended target) in the sample.

In this first example, the limiting forward primer contains a unique "5'-tag sequence". When the forward allele-discriminating primer binds to a mutant (−) template and initiates synthesis, the resulting (+) amplicon strand contains the entire forward primer sequence, including the 5'-tag sequence at its 5' end. Subsequently, these (+) amplicons serve as templates for the reverse allele-discriminating primer, or in the control experiment, the reverse conventional (non-discriminatory) primer. The resulting (−) amplicons will contain the complement of the 5'-tag sequence at their 3' ends. It is the 3' complement of the 5' tag sequence that is the target of the molecular beacon probes that are present in these reactions to light up the synthesized amplicons. Moreover, because the forward primer is present in limiting amount, single-stranded amplicons are made by extension of the excess reverse primer (either an allele-discriminatory primer or a conventional primer), ensuring that the molecular beacon probes can bind to their targets without competition from collapsing amplicon double strands. The sequences of the oligonucleotides used in this example were:

EGFR G719C SuperSelective Forward Primer 32-28-20/13-8:1:0

5'-ACCTGCCGTCAACACGTGCGCAGTAGACCATC-TCTCTTGAGGATCTTGAAGGAAACTGAA-CCTCTCCAACGAATCTCGAA-AAGTGCTGT-3' (SEQ ID No. 1), wherein the nucleotides of the 5'-tag are underlined, and the 3'-terminal interrogating nucleotide is bolded EGFR G719C SuperSelective Reverse Primer 24-18/10-8:1:0

5'-CCAGGGACCTTACCTTATACACCG-GATCCTAACTGAGGTCCA-ACCGGAGCA-3' (SEQ ID No. 2), wherein the 3'-terminal interrogating nucleotide is bolded EGFR Exon 18 Conventional Reverse Primer 5'-CCAGGGACCTTACCTTATACACCG-3' (SEQ ID No. 3)

Conventional Molecular Beacon (binds to the complement of the 5'-tag sequence)

5'-Quasar 670-CCGCCTG-ACCTGCCGTCAACACGTGCGCAGTAGACCATC-CAGGCGG-BHQ2-3', (SEQ ID No. 4), wherein the nucleotides in the single-stranded loop are underlined The target plasmids, containing either the EGFR G719C mutation or the corresponding EGFR wild-type sequence, were purchased from Integrated DNA Technologies, Coralville, Iowa (USA) and were prepared by inserting a 211-base-pair gene fragment into pIDTSmart Amp vectors. Mutant and wild-type plasmid DNA was digested with restriction endonuclease Sca I (New England Biolabs, Ipswich, Massachusetts (USA)). The digestion mixture contained 10 units Sca I and 4 μg of mutant or wild-type plasmid DNA in a 20-4 volume that contained 100 mM NaCl, 10 mM $MgCl_2$, 1 mM dithiothreitol, and 50 mM Tris-HCl (pH 7.9). The reaction was incubated for 120 min at 37° C., followed by incubation for 20 min at 80° C. to inactivate the endonuclease.

The PCR assays were performed in 30-μL volumes containing either 10,000 copies of the wild-type template, or 10 copies of the mutant template in a mixture containing 10,000 copies of the wild-type template, as well as amplification buffer (50 mM KCl, 10 mM Tris-HCl (pH 8.0), 2.5 mM $MgCl_2$), 50 mM tetramethylammonium chloride (Sigma-Aldrich, St. Louis, Missouri (USA)), 0.5% Tween 20 (Sigma-Aldrich), 1.5 Units Platinum Taq DNA polymerase (Thermo Fisher Scientific, Waltham, Massachusetts (USA)), 250 μM ATP, 250 μM CTP, 250 μM GTP, 250 μM TTP, and 300 nM conventional molecular beacon. One set of reactions contained 60 nM of EGFR G719C SuperSelective forward primer and 300 nM of EGFR Exon 18 conventional reverse primer. The other set of reactions contained 60 nM of EGFR G719C SuperSelective forward primer and 300 nM of EGFR G719C SuperSelective reverse primer. Both sets of reactions comprised duplicate amplifications of 10,000 wild-type copies and duplicate amplifications of 10 mutant copies in a mixture containing 10,000 wild-type copies. The amplifications were carried out in duplicate using 0.2 ml white polypropylene tubes (USA Scientific, Ocala, Florida (USA)) in a Bio-Rad CFX-96 Touch spectrofluorometric thermal cycler (Hercules, California (USA)). The thermal cycling program was 2 min at 95° C., followed by 55 cycles of 95° C. for 20 sec, 60° C. for 20 sec, and 72° C. for 20 sec. Molecular beacon fluorescence intensity was measured in real time at the end of the 60° C. annealing stage of each thermal cycle. Threshold cycles (Ct values) were calculated automatically by the thermal cycler.

Figure 2:
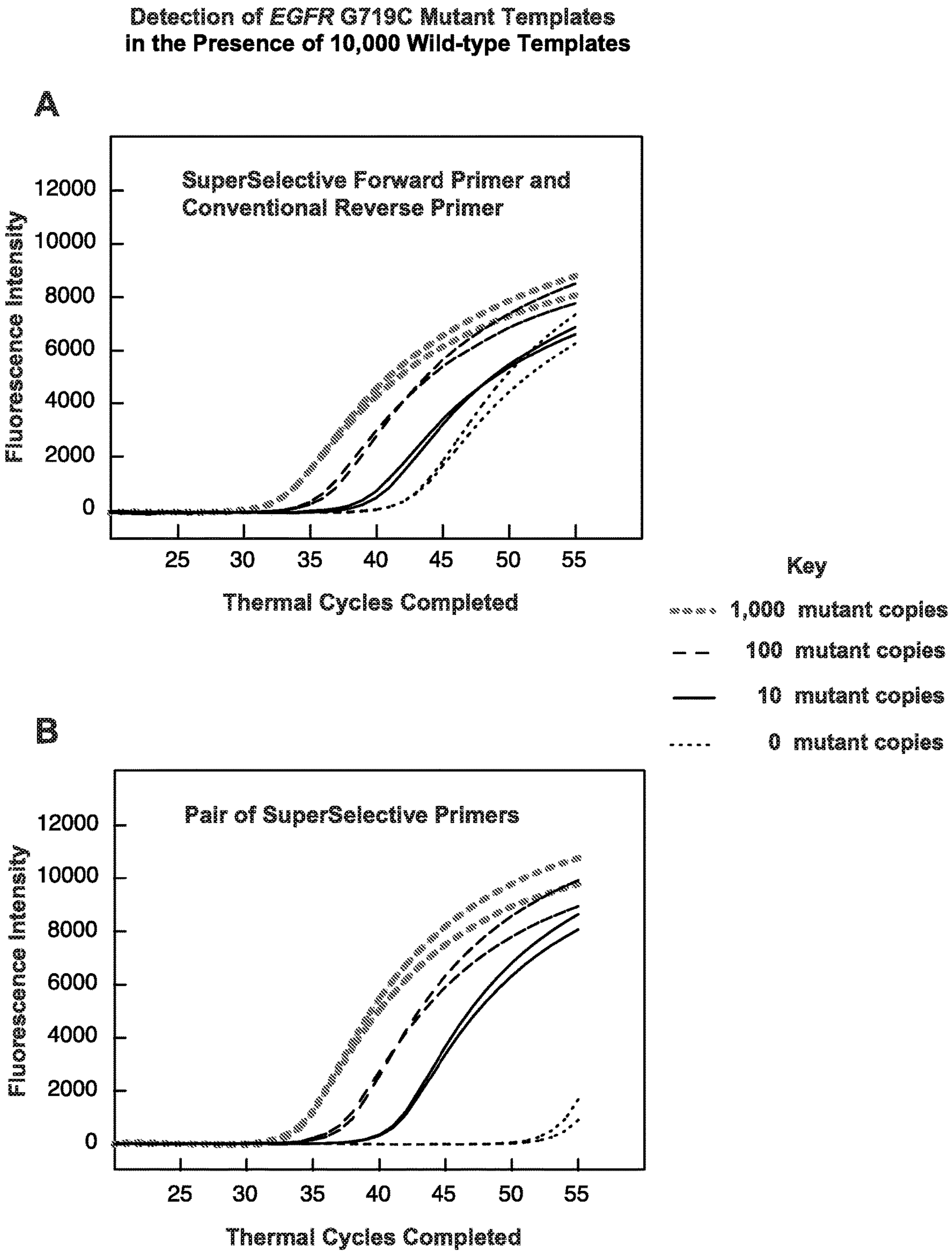
FIGS. 2A and 2B show the results of the real-time PCR assays of Example 1, wherein top panel A shows the results of amplification and detection utilizing a SuperSelective forward primer whose 3'-interrogating nucleotide is complementary to the mutant sequence and a conventional reverse primer that is complementary to both the mutant sequence and to its closely related wild-type sequence downstream from the target mutation; and bottom panel B shows the results of an otherwise identical real-time PCR assay that utilizes a pair of SuperSelective primers, both of whose 3'-interrogating nucleotides are complementary to the target mutation.

FIG. 2 shows the fluorescence intensity readings versus thermal cycles completed for these real-time PCR amplification and detection assays. Top panel A contains curves for the reactions utilizing the SuperSelective (SSP) forward primer and the conventional reverse primer, and bottom panel B contains curves for the reactions utilizing the SuperSelective (SSP) forward primer and the SuperSelective (SSP) reverse primer. Comparing assays containing 10 mutants in the presence of 10,000 wild types to assays containing only 10,000 wild types, the average threshold cycles (Ct values) of the duplicate amplifications, and the difference between average Ct values for those assays (ΔCt values), are listed in Table 1.

TABLE 1

| Primer Pair | Wild-type Ct | Wild-type + Mutant Ct | ΔCt |
|---|---|---|---|
| SSP + Conventional Reverse | 41.99 | 39.04 | 2.95 |
| SSP + SSP Reverse | 53.08 | 40.20 | 12.87 |

Example 2. Utilization of a Pair of SuperSelective Primers in Real-Time PCR Assays for the Detection of Rare EGFR T790M Mutant Templates in the Presence of Abundant Wild-Type Templates This example of methods of this invention utilizes the design shown in FIG. 3, which differs from the design of FIG. 1 regarding detection. In this example we utilized a molecular beacon variant sometimes called a "shared-stem" molecular beacon probe (Tsourkas et al. (2002) Nucleic Acids Research 30:4208-4215) to target the complement of the limiting SuperSelective primer's bridge sequence. Such a molecular beacon probe differs from a conventional molecular beacon probe (Example 1) in having the probe's target sequence complementary to one arm of the stem as well as to the single-stranded loop. The target-sequence mutation (T790M), which is located in Exon 20 of the EGFR gene, is a single base-pair substitution (SNP) of an A:T base pair in place of the G:C base pair that occurs in the otherwise identical closely related wild-type sequence. The sequences of the oligonucleotides used in this example were:

EGFR T790M SuperSelective Forward Primer 24-22/11-8:1:0

5'-CGCCTGCTGGGCATCTGCCTCACC-CAACACGTGCGCAGTAGACCAC-GCTCATCAT-3' (SEQ ID No. 5), wherein the 3'-terminal interrogating nucleotide is bolded, and the portion of the bridge sequence whose complement is detected by the shared-stem molecular beacon is underlined EGFR T790M SuperSelective Reverse Primer 23-10/19-7:1:0

5'-TTTGTGTTCCCGGACATAGTCCA-ATCTTCGGTG-GAGCTGCA-3' (SEQ ID No. 6), wherein the 3'-terminal interrogating nucleotide is bolded EGFR Exon 20 Conventional Reverse Primer 5'-TTTGTGTTCCCGGACATAGTCCA-3' (SEQ ID No. 7)

Shared-stem Molecular Beacon (binds to the complement of the bridge sequence of the forward primer)

5'-Quasar 670-TGGTCT-CAACACGTGCGCAGT-AGACCA-BHQ2-3' (SEQ ID No. 8), wherein the nucleotides in the loop and in the target-complementary arm are underlined Target plasmids containing either the EGFR T790M mutation or the corresponding EGFR wild-type sequence were purchased from Integrated DNA Technologies (IDT), and were prepared by inserting a 200-base-pair gene fragment into plDTSmart Amp vectors. Mutant and wild-type plasmid DNA was digested with restriction endonuclease Sca I. The digestion mixture contained 10 units Sca I and 4 μg of mutant or wild-type plasmid DNA in a 20-μL volume that contained 100 mM NaCl, 10 mM $MgCl_2$, 1 mM dithiothreitol, and 50 mM Tris-HCl (pH 7.9). The reaction was incubated for 120 min at 37° C., followed by incubation for 20 min at 80° C. to inactivate the endonuclease.

PCR assays were performed in 30-μL volumes containing 50 mM KCl, 10 mM Tris-HCl (pH 8.0), 2.5 mM $MgCl_2$, 50 mM tetramethylammonium chloride, 0.5% Tween 20, 1.5 Units Platinum Taq DNA polymerase, 250 μM ATP, 250 μM CTP, 250 μM GTP, 250 μM TTP, and 300 nM shared-stem molecular beacon. One set of reactions contained 60 nM of forward SuperSelective primer and 300 nM of conventional reverse primer. The other set of reactions contained 60 nM SuperSelective forward primer and 300 nM of SuperSelective reverse primer. Both sets or reactions comprised five replicate amplifications of 10,000 wild-type copies and five replicate amplifications of 10 mutant copies in a mixture containing 10,000 wild-type copies. The amplifications were carried out using 0.2 ml white polypropylene tubes in a Bio-Rad CFX-96 Touch spectrofluorometric thermal cycler. The thermal cycling program was 2 min at 95° C., followed by 55 cycles of 95° C. for 20 sec, 60° C. for 20 sec, and 72° C. for 20 sec. Molecular beacon fluorescence intensity was measured at the end of each 60° C. annealing stage. Threshold cycles were calculated automatically by the thermal cycler.

FIG. 4 shows the fluorescence intensity readings versus thermal cycles completed for the PCR amplification with real-time fluorescence detection. Top panel A contains curves for the replicate reactions utilizing the limiting SuperSelective (SSP) forward primer and the excess conventional reverse primer. Bottom panel B contains curves for the replicate reactions utilizing the limiting SuperSelective (SSP) forward primer and the excess SuperSelective (SSP) reverse primer. Comparing assays containing 10 mutants in the presence of 10,000 wild types to assays containing only 10,000 wild types, the average threshold cycles (Ct values) of the replicate amplifications, and the difference between average Ct values for those assays (ΔCt values), are listed in Table 2. The fluorescence intensity in three of the five amplifications of wild-type-only templates with the SuperSelective primer pair did not rise above background for 55 cycles, so we assigned each a Ct value of >55.

TABLE 2

| Primer Pair | Wild-type Ct | Wild-type + Mutant Ct | ΔCt |
|---|---|---|---|
| SSP + Conventional Reverse | 44.64 | 39.28 | 5.35 |
| SSP + SSP Reverse | >53.73 | 39.73 | >14.00 |

Example 3. Utilization of a Pair of SuperSelective Primers in Real-Time PCR Assays for the Determination of Whether Two Different Somatic Mutations in the Same Gene Occur in Cis on the Same Chromosome, or Whether they Occur in Trans on Sister Chromosomes This example of methods of this invention utilizes the method depicted in FIG. 5. Two different target mutations, T790M (which has an A:T base pair in place of a G:C base pair in Exon 20 of the EGFR gene) and C797S (which has a G:C base pair in place of a C:G base pair in the same exon) are located 20 nucleotides apart from each if they occur on the same chromosome, that is, if they occur in cis. The purpose of the assay shown in this example is to determine whether or not these two mutations (if they are both present in the sample) do indeed occur on the same chromosome, or whether (if they are both present) they occur on sister chromosomes, that is, whether they occur in trans.

We first carried out a series of preliminary assays that illustrate the type of results that would be obtained from a multiplex assay for these individual mutations (or from individual assays that each search for one or the other target mutation), the results of which would necessitate a cis-or-trans determination in order to identify an effective targeted therapy. In these assays, three primers were present: a SuperSelective forward primer for EGFR T790M, a SuperSelective forward primer for EGFR C797S, and a conventional reverse primer that participates in the synthesis of amplicons no matter whether just one of these two mutations is present in the sample or if both of these mutations are present in the sample. The sequences of the oligonucleotides used in these experiments were:

EGFR T790M SuperSelective Forward Primer 24-22/13-8:1:0

5'-GCCGCCTGCTGGGCATCTGCCTCA-AAGAAT-CAACAAGCTACAACTC-GCTCATCAT-3' (SEQ ID No. 9), wherein the 3'-terminal interrogating nucleotide is bolded EGFR C797S SuperSelective Forward Primer 21-13/20-9:1:0

5'-CTGCCTCACCTCCACCGTGCA-AGCACTCGCAGAA-CCTTCGGCTC-3' (SEQ ID No. 10), wherein the 3'-terminal interrogating nucleotide is bolded EGFR Exon 20 Conventional Reverse Primer #2

5'-CACCAGTTGAGCAGGTACTGG-3' (SEQ ID No. 11)

Amplicon-specific Molecular Beacon

5'-FAM-CCGTGG-CTGGACTATGTCCGG-GAACACA-CCACGG-BHQ1-3' (SEQ ID No. 12), wherein the nucleotides of the single-stranded loop are underlined In this first set of experiments (which served as a control), whose design is not shown in FIG. 5, both SuperSelective forward primers bind to the (−) template strand; the conventional reverse primer binds to the complementary (+) template strand downstream from where both forward primers bind in the complementary strand; and the molecular beacon probe binds to any resulting (−) amplicon strands in a region between the binding sites of the SuperSelective forward primers and the binding site of the conventional reverse primer.

As in the previous examples, the three target plasmids were purchased from Integrated DNA Technologies, and were prepared by inserting a 200-base-pair gene fragment into pIDTSmart Amp vectors. Each of these plasmid DNAs was digested with restriction endonuclease Sca I. The digestion mixture contained 10 units Sca I and 4 μg of mutant or wild-type plasmid DNA in a 20-4 volume that contained 100 mM NaCl, 10 mM $MgCl_2$, 1 mM dithiothreitol, and 50 mM Tris-HCl (pH 7.9). The reaction was incubated for 120 min at 37° C., followed by incubation for 20 min at 80° C. to inactivate the endonuclease.

We prepared five different amplification reaction mixtures in 30-4 volumes. Each contained 10,000 copies of wild-type DNA template. One set of reactions contained only the wild-type templates. The other four sets of reactions contained additionally 10 copies of one of the following target plasmids or plasmid combinations: T790M plasmids; C797S plasmids; T790M plasmids plus C797S plasmids (simulating the situation where these two mutations occur in trans); or T790M-C797S plasmids, having the two mutations present on the same template (in cis). All of the reaction mixtures contained 60 nM SuperSelective T790M forward primer, 60 nM C797S SuperSelective forward primer, 300 nM conventional reverse primer, 300 nM of an "amplicon-specific" molecular beacon, 50 mM KCl, 10 mM Tris-HCl (pH 8.0), 2.5 mM $MgCl_2$, 50 mM tetramethylammonium chloride (TMAC), 0.5% Tween 20, 1.5 Units Platinum Taq DNA polymerase, 250 μM ATP, 250 μM CTP, 250 μM GTP, and 250 μM TTP.

Four replicate amplifications of each of the five different reaction mixtures were carried out using 0.2 ml white polypropylene tubes in a Bio-Rad CFX-96 Touch spectrofluorometric thermal cycler. The thermal cycling program was 2 min at 95° C., followed by 55 cycles of 95° C. for 20 sec, 60° C. for 20 sec, and 72° C. for 20 sec. Molecular beacon fluorescence intensity was measured at the end of each 60° C. annealing stage.

FIG. 6 shows the fluorescence intensity readings versus thermal cycles for the PCR amplifications with real-time fluorescence detection. As stated above, all amplification reaction mixtures contained 10,000 wild-type copies (the unintended target template). Top left-hand panel A shows the results of the replicate reactions in which the amplification reaction mixture also contained 10 copies of the T790M mutant target template; top right-hand panel B shows the results of the replicate reactions in which the amplification reaction mixture also contained 10 copies of the C797S mutant target template; middle left-hand panel C shows the results of the replicate reactions in which the amplification reaction mixture also contained 10 copies of the T790M mutant target template and 10 copies of the T790M-C797S mutant target template; middle right panel D shows the results of the replicate reactions in which the amplification reaction mixture also contained 10 copies of the T790M mutant target template and 10 copies of the C797S mutant target template; and bottom panel E shows the results of the replicate reactions in which the amplification reaction mixture contained no copies of any mutant target template. Average threshold cycles (Ct values) of these replicate amplifications are listed in Table 3.

TABLE 3

| Templates in the Reaction Mixture | Ct |
|---|---|
| 10,000 Wild types + 0 Mutants | 45.82 |
| 10,000 Wild types + 10 Copies of T790M | 38.34 |
| 10,000 Wild types + 10 Copies of C797S | 39.95 |
| 10,000 Wild types + 10 Copies of T790M + 10 copies C797S (trans) | 38.44 |
| 10,000 Wild types + 10 Copies of T790M-C797S (cis) | 39.49 |

Table 3 shows the results of the control reactions that contained EGFR T790M SuperSelective forward primers and EGFR C797S SuperSelective forward primers and EGFR Exon 20 conventional reverse primers. The average Ct value for the sample containing only wild-type (45.82) was distinguishable from the sample containing the two mutations in cis (39.49). However, this average Ct value was virtually identical to the average Ct value of the reactions that contained the two mutations in trans, and was virtually identical to the average Ct values of the reactions that contained only one of the two different mutations.

To illustrate how to determine whether these two mutations occur on the same templates (i.e., in cis), according to an embodiment of this invention, we performed three additional sets of assays, whose design is illustrated in FIG. 5. These assays contain a limited EGFR T790M SuperSelective forward primer, an excess EGFR C797S reverse primer, and an interprimer-specific molecular beacon probe that targets a region of the (−) amplicons between the sequences to which the SuperSelective primers bind, thereby signaling only when both primers have bound and been extended on template molecules that contain both the EGFR T790M mutation and the EGFR C797S mutation (i.e., only when the two mutations are present in cis). The oligonucleotides utilized were:

EGFR T790M SuperSelective Forward Primer 24-22/13-8:1:0

5'-GCCGCCTGCTGGGCATCTGCCTCA-AAGAAT-CAACAAGCTACAACTC-GCTCATCAT-3' (SEQ ID NO. 9), wherein the 3'-terminal interrogating nucleotide is bolded EGFR C797S SuperSelective Reverse Primer 30-20/19-8:1:0

5'-TTGAGCAGGTACTGGGAGCCAATATTGTCT-GTCCTTTACAAGCACGAGTG-CCAGGAGGG-3' (SEQ ID No. 13), wherein the 3'-terminal interrogating nucleotide is bolded Interprimer-specific Molecular Beacon 5'-FAM-CCGTCG-CAGCTCATGCCCTTCGGC-CGACGG-BHQ1-3' (SEQ ID No. 14), wherein the nucleotides of the single-stranded loop are underlined The amplification reaction mixtures contained 60 nM SuperSelective forward primer, 300 nM SuperSelective reverse primer, and 300 nM molecular beacon. All reaction mixtures contained 10,000 copies of the EGFR wild-type target template. One set of reactions contained additionally 10 copies of the T790M-C797S target template, a second set of reactions contained 10 copies of the T790M target template and 10 copies of the C797S target template, and a third set of reactions contained no copies of either mutant target template, that is, only the wild-type templates were present. Otherwise the amplification reaction mixtures were as described above.

Four replicate amplifications of each of the three reaction mixtures with real-time detection were carried out as described above. Real-time fluorescence readings obtained during the first 55 amplification cycles are shown in three graphs comprising FIG. 7. Bottom panel C shows the results from the reaction mixtures containing only 10,000 wild-type templates, in which the fluorescence of all four replicates failed to rise above background through 55 cycles; so the average Ct of the four replicates, while not determinable, was at least greater than 55. Top right-hand panel B shows the results from the reaction mixtures containing 10,000 wild-type templates plus ten copies each of the T790M template and the C797S template (i.e., the two mutations were present in trans); and fluorescence of all four replicates failed to rise above background through 55 cycles, so the average Ct of the four replicates, while not determinable, was at least greater than 55. Top left-hand panel A shows the results from the reaction mixtures containing 10,000 wild-type templates plus ten copies of the T790M-C797S template (i.e., the two mutations were present in cis); and all four of these reactions gave a positive signal, with an average Ct of 41.31. The ΔCt between ten cis templates in the presence of 10,000 wild-type templates, while not precisely determinable, was thus at least greater than 13.69, when compared to reactions containing ten copies each of the two different mutant templates present in trans in reactions that also contained 10,000 wild-type templates.

Example 4. Utilization of a SuperSelective Primer as the Limiting Primer with an ARMS Reverse Primer in Real-Time PCR Assays for the Determination of Whether Two Different Somatic Mutations in the Same Gene Occur in Cis on the Same Chromosome, or Whether they Occur in Trans on Two Different Sister Chromosomes We repeated the method described in Example 3 utilizing an ARMS primer as the reverse primer in place of the reverse SuperSelective primer. This alternative arrangement is illustrated in FIG. 8. The oligonucleotides in the amplification reaction mixture were:

EGFR T790M SuperSelective Forward Primer 24-22/13-8:1:0

5'-GCCGCCTGCTGGGCATCTGCCTCA-AAGAAT-CAACAAGCTACAACTC-GCTCATCAT-3' (SEQ ID No. 9), wherein the 3'-terminal interrogating nucleotide is bolded EGFR C797S ARMS Reverse Primer 19:m1:1:1:0

5'-TCCCGGACATAGTCCAGGAAGG-3' (SEQ ID No. 15), wherein the 3'-terminal interrogating nucleotide is bolded and the introduced mismatched nucleotide is bolded and italicized Interprimer-specific Molecular Beacon 5'-FAM-CCGTCG-CAGCTCATGCCCTTCGGC-CGACGG-BHQ1-3' (SEQ ID No. 14), wherein the nucleotides of the single-stranded loop are underlined In the sequence of the ARMS primer the deliberately introduced nucleotide that is mismatched to both the intended (mutant) target sequence and to the closely related unintended (wild-type) target sequence is bolded and italicized. That nucleotide is the third nucleotide from the 3' end, and it creates an A:C mismatch with respect to both the intended target sequence and the unintended closely related target sequence.

Except for the substitution of an ARMS reverse primer for the SuperSelective reverse primer, the reaction mixtures were the same as described in Example 3, as were the thermal cycling conditions and the manner of fluorescence detection. The design of this experiment is illustrated in FIG. 8. For the same series of amplifications as were shown in FIG. 7, very similar results were obtained.

Figure 9:
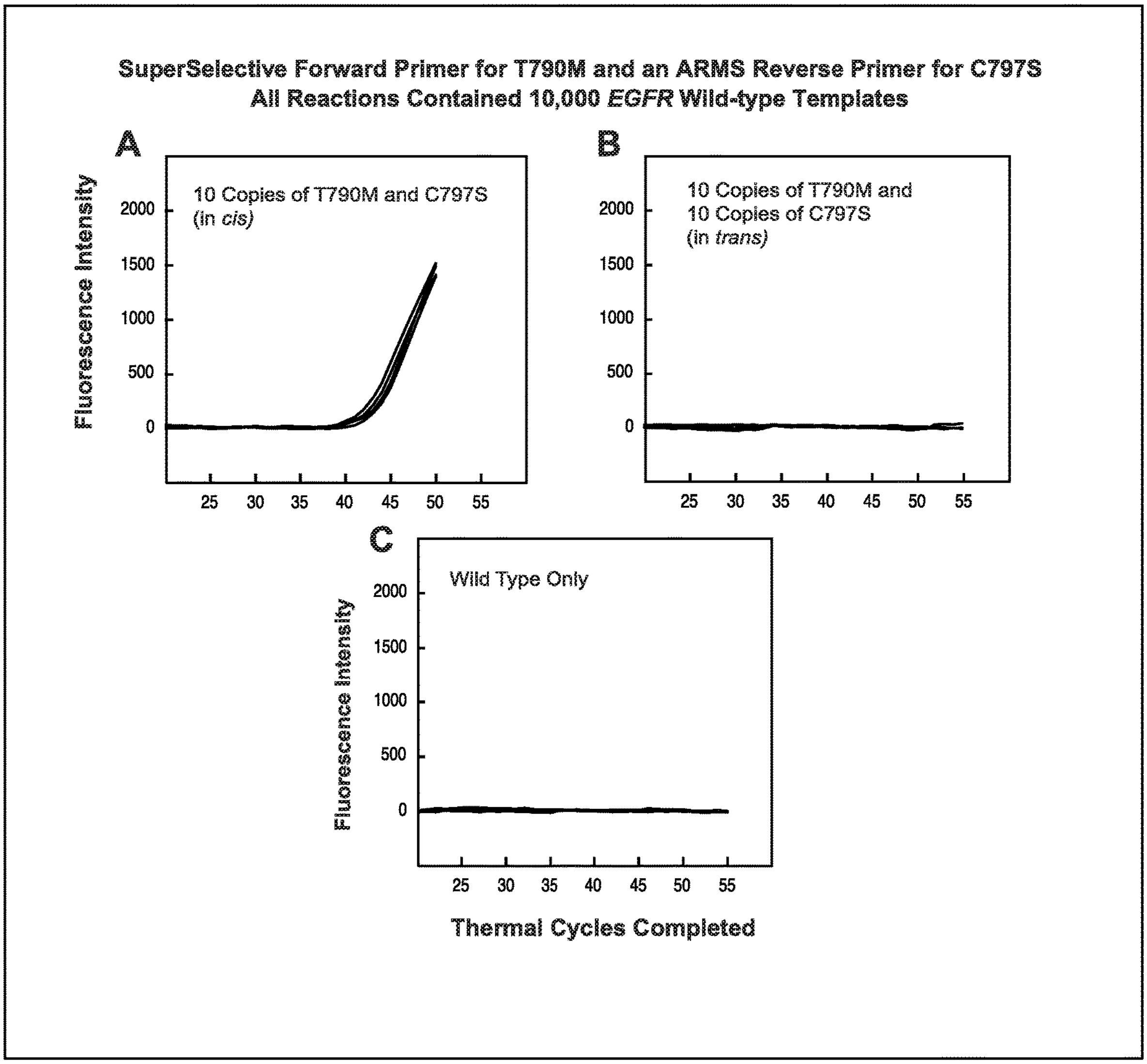
FIGS. 9A, 9B, and 9C show the results of the real-time PCR assays of Example 4, wherein the reaction mixtures contain a SuperSelective forward primer for the EGFR T790M mutation, and an ARMS reverse primer for the EGFR C797S mutation. (A) 10 copies of T790M and of C797S (in cis), (B) 10 copies of T790M and 10 copies of C797S (in trans), and (C) wild type only.

The results of these experiments that included an ARMS primer are shown in FIG. 9. For reactions containing only 10,000 wild-type templates, the fluorescence signal from all four replicates failed to rise above background through 55 cycles, so the average Ct value of the four replicates, while not determinable, was at least greater than 55. For the reactions that contained 10,000 wild-type templates plus ten copies each of the T790M template and the C797S template (present in trans), the fluorescence signal from all four replicates failed to rise above background through 55 cycles, so the average Ct value of all four replicates, while not determinable, was at least greater than 55. For the reactions that contained 10,000 wild-type templates plus ten copies of the T790M-C797S template (present in cis), the average Ct value of the four replicates was 43.31. The ΔCt value between the reactions containing ten cis templates and 10,000 wild-type templates and the reactions containing ten trans templates and 10,000 wild-type templates, while not precisely determinable, was thus at least greater than 11.69.

Example 5. Comparison of the Utilization of a SuperSelective Primer as the Limiting Primer or the Excess Primer in Real-Time PCR Assays that Include an ARMS Primer for the Detection of Rare KRAS G12D Mutant Templates in the Presence of Abundant Wild-Type Templates Experiments in this example utilized a SuperSelective primer as the limiting first primer (here described as the forward primer) and an ARMS primer as the excess second primer (here described as the reverse primer); and a SuperSelective primer as the excess first primer (here described as the reverse primer) and an ARMS primer as the limiting second primer (here described as the forward primer). For comparison, the experiments also utilized a pair of SuperSelective primers. In all primer pairs the forward limiting primer has a 5'-tag sequence whose complementary sequence is the target for a molecular beacon probe. The method in which the SuperSelective primer is the reverse primer and the ARMS primer is the forward primer is depicted in FIG. 10, wherein the ARMS forward primer includes a 5'-tag sequence. The intended target in this example is a KRAS G12D mutant template, which differs from the closely related wild-type template by a single T:A mutant base pair. Both primers in every pair have a 3'-terminal interrogating nucleotide that is complementary to a nucleotide of that base pair. The sequences of the oligonucleotides used in this example were:

KRAS G12D SuperSelective Forward Primer 32-28-19/10-8:1:0

5'-ACCTGCCGTCAACACGTGCGCAGTAGAC-CATC-GGCCTGCTGAAAATGACT-GAATATAAAC-ACACAGTCTGAGCCCACTC-TG-GAGCTGA-3' (SEQ ID No. 16), wherein the nucleotides in the 5'-tag sequence are underlined and the 3'-terminal interrogating nucleotide is bolded KRAS G12D SuperSelective Reverse Primer 30-14/11-7:1:0

5'-AAATGATTCTGAATTAGCTGTATCGTCAAG-TACCCAGCTACTAA-TACGCCAT-3' (SEQ ID No. 17), wherein the 3'-terminal interrogating nucleotide is bolded Conventional Molecular Beacon for use with the SuperSelective Forward Primer (binds to the complement of the 5'-tag sequence)

5'-Quasar 670-CCGCCTG-ACCTGCCGT-CAACACGTGCGCAGTAGACCATC-CAGGCGG-BHQ2-3' (SEQ ID No. 4), wherein the nucleotides in the single-stranded loop are underlined KRAS G12D ARMS Forward Primer 21-21-m1:1:1:0

5'-CAACACTGGCGCAGTAGACCA-TAAACTTGTGGTAGTTGGAGC GGA-3' (SEQ ID No. 18), wherein the nucleotides in the 5'-tag sequence are underlined, the 3'-terminal interrogating nucleotide is bolded, and an introduced mismatched nucleotide is italicized and bolded KRAS G12D ARMS Reverse Primer 18-m1:1:1:0

5'-AGGCACTCTTGCCTACGCCAT-3' (SEQ ID No. 19), wherein the 3'-terminal interrogating nucleotide is bolded, and an introduced mismatched nucleotide is italicized and bolded Shared-stem Molecular Beacon for use with the ARMS Forward Primer (binds to the complement of the 5'-tag sequence)

5'-FAM-TGGTCT-CAACACTGGCGCAGT-AGACCA-BHQ1-3' (SEQ ID No. 20), wherein the nucleotides in the single-stranded loop are underlined The third nucleotide from the 3' end of each ARMS primer is bolded and italicized, because it was mismatched both to the mutant sequence and to the wild-type sequence. This mismatch is indicated by an "m" in the sequence designation.

The target plasmids, containing either the KRAS G12D mutation or the corresponding KRAS wild-type sequence, were purchased from Integrated DNA Technologies, and were prepared by inserting a 390-base-pair gene fragment into pUCIDT vectors. Mutant and wild-type plasmid DNAs were digested with restriction endonuclease Dra I (New England Biolabs). The digestion mixture contained 10 units Dra I and 4 μg of mutant or wild-type plasmid DNA in a 20-μL volume that contained 50 mM potassium acetate, 20 mM Tris-acetate (pH 7.9), 10 mM magnesium acetate, and 100 μg/ml bovine serum albumin. The reaction was incubated for 120 min at 37° C., followed by incubation for 20 min at 65° C. to inactivate the endonuclease.

The PCR assays were performed in 30-μL volumes containing 50 mM KCl, 10 mM Tris-HCl (pH 8.0), 2.5 mM $MgCl_2$, 50 mM tetramethylammonium chloride (Sigma-Aldrich), 0.5% Tween 20 (Sigma-Aldrich), 1.5 Units Platinum Taq DNA polymerase (Thermo Fisher Scientific), 250 μM ATP, 250 μM CTP, 250 μM GTP, 250 μM TTP, 60 nM forward primer, 300 nM reverse primer and 300 nM of the conventional molecular beacon for use with the SuperSelective forward primer or 300 nM of the shared-stem molecular beacon for use with the ARMS forward primer. The amplifications were carried out using 0.2 ml white polypropylene tubes (USA Scientific) in a Bio-Rad CFX-96 Touch spectrofluorometric thermal cycler. The thermal cycling program was 2 min at 95° C., followed by 55 cycles of 95° C. for 20 sec, 60° C. for 20 sec, and 72° C. for 20 sec. Molecular beacon fluorescence intensity was measured at the end of each 60° C. annealing stage.

The reaction mixtures contained 10,000 copies of the wild-type target templates and either 10 or 0 copies of the mutant target templates. The amplification reactions were run in triplicate. The resulting real-time fluorescence results are shown in FIG. 11, where top panel A shows the results obtained for the pair of SuperSelective primers, bottom left-hand panel B shows the results obtained for the pair of primers that includes a SuperSelective forward limiting primer and an excess ARMS reverse primer, and bottom right-hand panel C shows the results obtained for the pair of primers that includes a limiting ARMS forward primer and an excess SuperSelective reverse primer. In none of the panels did the fluorescence of the wild-type samples rise above background through 55 cycles, whereas all samples with 10 copies of the mutant template had Ct values below 45.

Example 6. Duplex Assay: Utilization of a Pair of SuperSelective Primers in Real-Time PCR Assays for the Detection of Rare EGFR G719C Mutant Templates in the Presence of Abundant Normal Human Genomic DNA Templates, as Well as the Simultaneous Utilization of a Different SuperSelective Primer and a Conventional Primer for the Detection of the β-Actin Reference Gene The design of these PCR assays for the detection of G719C is shown in FIG. 12. The G719C target mutation, which is located in Exon 21 of the human epidermal growth factor receptor (EGFR) gene, is a T:A base pair in place of the G:C base pair that occurs in the otherwise identical wild-type gene sequence. The assay utilizes a linearized plasmid containing the mutant target sequence, and the assay utilizes fragmented normal human genomic DNA that contains the wild-type EGFR gene sequence to simulate the cell-free DNA fragments that are isolated from the blood plasma in a liquid biopsy sample.

In this example, the limiting forward primer for the detection of G719C contains a unique "5'-tag sequence". When the forward allele-discriminating primer binds to a mutant (−) template and initiates synthesis, the resulting (+) amplicon strand contains the entire forward primer sequence, including the 5'-tag sequence at its 5' end. Subsequently, these (+) amplicons serve as templates for the reverse allele-discriminating primer. The resulting (−) amplicons contain the complement of the 5'-tag sequence at their 3' ends. It is the 3' complement of the 5'-tag sequence that is the target for the binding of FAM-labeled conventional molecular beacon probes. The forward SuperSelective primer is present in a limiting concentration, and the reverse SuperSelective primer is present in an excess concentration, ensuring that the molecular beacon probes will be able to bind to the excess (−) amplicon targets without significant competition from the limited concentration of (+) amplicons.

Furthermore, the detection of the β-actin reference gene sequence, that occurs in normal human DNA (containing the wild-type EGFR gene), was included in the assay to provide a reference threshold value (Ct) that reflects the amount of DNA in the sample. The amplicons were detected using a Quasar 705-labeled interprimer-specific molecular beacon that binds to the excess β-actin (−) amplicons between the complement of the sequence of the SuperSelective primer and the sequence of the conventional primer.

The sequences of the oligonucleotides used in this example were:

EGFR G719C SuperSelective Forward Primer 32-28-20/13-8:1:0

5'-ACGTGCCCTCAATACGAGCCCCTTCACCAAC-TCTCTTGAGGATCTTGAAGGAAACTGAA-CCTCTCCAACGAATCTCGAA-AAGTGCTGT-3' (SEQ ID No. 21), wherein the nucleotides of the 5'-tag are underlined, and the 3'-terminal interrogating nucleotide is bolded EGFR G719C SuperSelective Reverse Primer 24-18/10-7:1:0

5'-CCAGGGACCTTACCTTATACACCG-GATCCTAACTGAGGTCCA-ACCGGAGCA-3' (SEQ ID No. 2), wherein the 3'-terminal interrogating nucleotide is bolded Conventional Molecular Beacon (binds to the complement of the 5'-tag sequence)

5'-FAM-CGCCTG-ACGTGCCCT-CAATACGAGCCCCCTTCACCAAC-CAGGCG-BHQ1-3', (SEQ ID No. 22), wherein the nucleotides in the single-stranded loop are underlined β-actin SuperSelective Forward Primer 24-18/14-9:0

5'-CCAACCGCGAGAAGATGACCCAGG-CAT-AGCCAGCTAATGACC-CCTCTTCTG-3' (SEQ ID No. 23)

β-actin Conventional Reverse Primer

5'-CGGCTA-AGAGAACCAGTGAGAAAGGGC-3' (SEQ ID No. 24), with a 5' tail sequence interprimer-specific Molecular Beacon (binds in the inter-primer region of the amplicons)

5'-Quasar 705-CCGCTC-CCTCCTTCCTGGCCTCCC-GAGCGG-BHQ2-3', (SEQ ID No. 25), wherein the nucleotides in the single-stranded loop are underlined The target plasmid containing the EGFR G719C mutation was purchased from Integrated DNA Technologies, and it was prepared by inserting a 211-base-pair gene fragment into pUCIDT vectors. The mutant plasmid DNA was digested with restriction endonuclease Dra I (New England Biolabs). The digestion mixture contained 10 units Dra I and 4 μg of mutant plasmid DNA in a 20-μL volume that contained 50 mM potassium acetate, 20 mM Tris-acetate (pH 7.9), 10 mM magnesium acetate, and 100 μg/ml bovine serum albumin. The reaction was incubated for 120 min at 37° C., followed by incubation for 20 min at 65° C. to inactivate the endonuclease.

Wild-type human DNA (from multiple anonymous donors), catalog number G1521, was purchased from the Promega Corporation (Madison, WI). Approximately 9 μg of this DNA was digested for 120 minutes at 37° C. in 50 μL containing 10 units of restriction endonuclease Mse I (New England Biolabs, Ipswich, MA) in a buffer provided by New England Biolabs that contained 100 μg/mL bovine serum albumin, 10 mM magnesium acetate, 50 mM potassium acetate, and 20 mM Tris-acetate (pH 7.9); followed by incubation for 20 minutes at 65° C. to inactivate the enzyme.

The PCR assays were performed in 30-μL volumes containing 50 mM KCl, 10 mM Tris-HCl (pH 8.0), 2.5 mM $MgCl_2$, 60 mM tetramethylammonium chloride (Sigma-Aldrich), 0.5% Tween 20 (Sigma-Aldrich), 1.5 Units Platinum Taq DNA polymerase (Thermo Fisher Scientific), 250 μM ATP, 250 μM CTP, 250 μM GTP, 250 μM TTP, 60 nM of each of the two different SuperSelective forward primers, 500 nM EGFR G719C SuperSelective reverse primer, 500 nM β-actin conventional reverse primer, 300 nM conventional molecular beacon for the detection of the EGFR G719C mutant amplicons, and 500 nM interprimer-specific molecular beacon for the detection of the β-actin amplicons.

The amplifications were carried out using 0.2 ml white polypropylene tubes (USA Scientific) in a Bio-Rad CFX-96 Touch spectrofluorometric thermal cycler. The thermal cycling program was 2 min at 95° C., followed by 55 cycles of 95° C. for 20 sec, 60° C. for 20 sec, and 72° C. for 20 sec. Molecular beacon fluorescence intensity was measured in both the FAM channel and in the Quasar 705 channel at the end of each 60° C. annealing stage.

FIG. 13 shows the fluorescence intensity readings versus thermal cycles

A first set of 10 reactions (whose results are shown in the upper left-hand panel A) contained 10,000 copies of wild-type genomic DNA plus 500 copies of mutant plasmid DNA; a second set of 10 reactions (whose results are shown in the upper right-hand panel B) contained 10,000 copies of wild-type genomic DNA plus 50 copies of mutant plasmid DNA; a third set of 10 reactions (whose results are shown in the lower left-hand panel C) contained 10,000 copies of wild-type genomic DNA plus 5 copies of mutant plasmid DNA; and a fourth set of 10 reactions (whose results are shown in the lower right-hand panel D) contained only 10,000 copies of wild-type genomic DNA and no copies of mutant plasmid DNA.

The foregoing examples and description of preferred embodiments should be taken as illustrating rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

The invention claimed is:

1. A primer-dependent amplification and detection method that is capable of amplifying and detecting in a sample as few as ten copies of at least one rare DNA intended target sequence ("rare target sequence") in a mixture containing, for each rare target sequence, 10,000 copies of an unintended target sequence that differs from the rare target sequence by as little as one or two base pairs, comprising:

(a) preparing a primer-dependent amplification reaction mixture that includes the sample, a DNA polymerase, deoxyribonucleoside triphosphates, an amplification buffer, homogeneous fluorescence detection means for detecting amplification products, and for each rare target sequence a pair of primers consisting of a forward primer and a reverse primer that are specific for the rare target sequence but mismatched to the unintended target sequence, (b) repeatedly cycling the primer-dependent amplification reaction mixture by said primer-dependent amplification method to amplify each rare target sequence present in the sample, and (c) detecting that rare target sequence by measuring the intensity of fluorescence from the homogeneous fluorescence detection means;

wherein (i) only two primers are utilized for the detection of each mutation in a rare target sequence and (ii) the forward primer is a SuperSelective primer comprising from the 5' end to the 3' end a first anchor sequence, a first bridge sequence, and a first foot sequence that is mismatched to the unintended target sequence by at least its 3'-terminal or 3'-penultimate nucleotide, and (iii) the reverse primer is a SuperSelective primer comprising from the 5' end to the 3' end a second anchor sequence, a second bridge sequence, and a second foot sequence that is mismatched to the complement of the unintended target sequence by at least its 3'-terminal or 3'-penultimate nucleotide, and (iv) wherein the pair of primers only initiates synthesis beyond the site where the mutation in the rare target sequence is present.

2. The method according to claim 1, wherein each SuperSelective primer contains a 3'-terminal interrogating nucleotide that is complementary to the rare target sequence but mismatched to the unintended target sequence.

3. The method according to claim 1, wherein said cycling comprises temperature cycling in a non-symmetric polymerase chain reaction (PCR) method.

4. The method according to claim 3, wherein said detecting comprises real-time detection.

5. The method according to claim 1, wherein the at least one rare target sequence in the sample includes at least two different rare target sequences, and the homogeneous fluorescence detection means comprises at least two different homogeneous fluorescence detection probes for the at least two different rare target sequences, respectively.

6. The method according to claim 5, wherein the at least two rare target sequences include a group of rare target sequences, and the probes for the rare target sequences in the group are labeled with the same color.

7. The method according to claim 5, wherein each probe comprises a sequence that is complementary to the complement of the first bridge sequence or of the second bridge sequence.

8. The method according to claim 1, wherein each different unintended target sequence differs from its corresponding rare target sequence by a single base pair, and both the SuperSelective forward primers and the SuperSelective reverse primers are mismatched to that single base pair.

9. The method according to claim 8, wherein the homogeneous fluorescence detection means comprises a probe for each rare target sequence.

10. The method according to claim 9, wherein the SuperSelective forward or SuperSelective reverse primer for each rare target sequence contains a 5'-tag sequence, and wherein the complement of each 5'-tag sequence is the target of the probe.

11. The method according to claim 1, wherein the pair of primers together initiates synthesis of one amplicon.

* * * * *

SEQUENCE LISTING

```
<160> NUMBER OF SEQ ID NOS: 25

<210> SEQ ID NO 1
<211> LENGTH: 89
<212> TYPE: DNA
<213> ORGANISM: Artificial
<220> FEATURE:
<223> OTHER INFORMATION: Synthetic

<400> SEQUENCE: 1

acctgccgtc aacacgtgcg cagtagacca tctctcttga ggatcttgaa ggaaactgaa     60

cctctccaac gaatctcgaa aagtgctgt                                       89
```

<210> SEQ ID NO 2
<211> LENGTH: 51
<212> TYPE: DNA
<213> ORGANISM: Artificial
<220> FEATURE:
<223> OTHER INFORMATION: Synthetic

<400> SEQUENCE: 2
ccagggacct taccttatac accggatcct aactgaggtc caaccggagc a 51

<210> SEQ ID NO 3
<211> LENGTH: 24
<212> TYPE: DNA
<213> ORGANISM: Artificial
<220> FEATURE:
<223> OTHER INFORMATION: Synthetic

<400> SEQUENCE: 3
ccagggacct taccttatac accg 24

<210> SEQ ID NO 4
<211> LENGTH: 46
<212> TYPE: DNA
<213> ORGANISM: Artificial
<220> FEATURE:
<223> OTHER INFORMATION: Synthetic

<400> SEQUENCE: 4
ccgcctgacc tgccgtcaac acgtgcgcag tagaccatcc aggcgg 46

<210> SEQ ID NO 5
<211> LENGTH: 55
<212> TYPE: DNA
<213> ORGANISM: Artificial
<220> FEATURE:
<223> OTHER INFORMATION: Synthetic

<400> SEQUENCE: 5
cgcctgctgg gcatctgcct cacccaacac gtgcgcagta gaccacgctc atcat 55

<210> SEQ ID NO 6
<211> LENGTH: 41
<212> TYPE: DNA
<213> ORGANISM: Artificial
<220> FEATURE:
<223> OTHER INFORMATION: Synthetic

<400> SEQUENCE: 6
tttgtgttcc cggacatagt ccaatcttcg gtggagctgc a 41

<210> SEQ ID NO 7
<211> LENGTH: 23
<212> TYPE: DNA
<213> ORGANISM: Artificial
<220> FEATURE:
<223> OTHER INFORMATION: Synthetic

<400> SEQUENCE: 7
tttgtgttcc cggacatagt cca 23

<210> SEQ ID NO 8
<211> LENGTH: 27
<212> TYPE: DNA
<213> ORGANISM: Artificial
<220> FEATURE:

<223> OTHER INFORMATION: Synthetic

<400> SEQUENCE: 8
tggtctcaac acgtgcgcag tagacca 27

<210> SEQ ID NO 9
<211> LENGTH: 55
<212> TYPE: DNA
<213> ORGANISM: Artificial
<220> FEATURE:
<223> OTHER INFORMATION: Synthetic

<400> SEQUENCE: 9
gccgcctgct gggcatctgc ctcaaagaat caacaagcta caactcgctc atcat 55

<210> SEQ ID NO 10
<211> LENGTH: 44
<212> TYPE: DNA
<213> ORGANISM: Artificial
<220> FEATURE:
<223> OTHER INFORMATION: Synthetic

<400> SEQUENCE: 10
ctgcctcacc tccaccgtgc aagcactcgc agaaccttcg gctc 44

<210> SEQ ID NO 11
<211> LENGTH: 21
<212> TYPE: DNA
<213> ORGANISM: Artificial
<220> FEATURE:
<223> OTHER INFORMATION: Synthetic

<400> SEQUENCE: 11
caccagttga gcaggtactg g 21

<210> SEQ ID NO 12
<211> LENGTH: 34
<212> TYPE: DNA
<213> ORGANISM: Artificial
<220> FEATURE:
<223> OTHER INFORMATION: Synthetic

<400> SEQUENCE: 12
ccgtggctgg actatgtccg ggaacacacc acgg 34

<210> SEQ ID NO 13
<211> LENGTH: 59
<212> TYPE: DNA
<213> ORGANISM: Artificial
<220> FEATURE:
<223> OTHER INFORMATION: Synthetic

<400> SEQUENCE: 13
ttgagcaggt actgggagcc aatattgtct gtcctttaca agcacgagtg ccaggaggg 59

<210> SEQ ID NO 14
<211> LENGTH: 30
<212> TYPE: DNA
<213> ORGANISM: Artificial
<220> FEATURE:
<223> OTHER INFORMATION: Synthetic

<400> SEQUENCE: 14
ccgtcgcagc tcatgccctt cggccgacgg 30

<210> SEQ ID NO 15
<211> LENGTH: 22
<212> TYPE: DNA
<213> ORGANISM: Artificial
<220> FEATURE:
<223> OTHER INFORMATION: Synthetic

<400> SEQUENCE: 15
tcccggacat agtccaggaa gg 22

<210> SEQ ID NO 16
<211> LENGTH: 88
<212> TYPE: DNA
<213> ORGANISM: Artificial
<220> FEATURE:
<223> OTHER INFORMATION: Synthetic

<400> SEQUENCE: 16
acctgccgtc aacacgtgcg cagtagacca tcggcctgct gaaaatgact gaatataaac 60
acacagtctg agcccactct ggagctga 88

<210> SEQ ID NO 17
<211> LENGTH: 52
<212> TYPE: DNA
<213> ORGANISM: Artificial
<220> FEATURE:
<223> OTHER INFORMATION: Synthetic

<400> SEQUENCE: 17
aaatgattct gaattagctg tatcgtcaag tacccagcta ctaatacgcc at 52

<210> SEQ ID NO 18
<211> LENGTH: 45
<212> TYPE: DNA
<213> ORGANISM: Artificial
<220> FEATURE:
<223> OTHER INFORMATION: Synthetic

<400> SEQUENCE: 18
caacactggc gcagtagacc ataaacttgt ggtagttgga gcgga 45

<210> SEQ ID NO 19
<211> LENGTH: 21
<212> TYPE: DNA
<213> ORGANISM: Artificial
<220> FEATURE:
<223> OTHER INFORMATION: Synthetic

<400> SEQUENCE: 19
aggcactctt gcctacgcca t 21

<210> SEQ ID NO 20
<211> LENGTH: 27
<212> TYPE: DNA
<213> ORGANISM: Artificial
<220> FEATURE:
<223> OTHER INFORMATION: Synthetic

<400> SEQUENCE: 20
tggtctcaac actggcgcag tagacca 27

<210> SEQ ID NO 21
<211> LENGTH: 89
<212> TYPE: DNA
<213> ORGANISM: Artificial
<220> FEATURE:

-continued

<223> OTHER INFORMATION: Synthetic

<400> SEQUENCE: 21
acgtgccctc aatacgagcc cccttcacca actctcttga ggatcttgaa ggaaactgaa 60
cctctccaac gaatctcgaa aagtgctgt 89

<210> SEQ ID NO 22
<211> LENGTH: 44
<212> TYPE: DNA
<213> ORGANISM: Artificial
<220> FEATURE:
<223> OTHER INFORMATION: Synthetic

<400> SEQUENCE: 22
cgcctgacgt gccctcaata cgagccccct tcaccaacca ggcg 44

<210> SEQ ID NO 23
<211> LENGTH: 51
<212> TYPE: DNA
<213> ORGANISM: Artificial
<220> FEATURE:
<223> OTHER INFORMATION: Synthetic

<400> SEQUENCE: 23
ccaaccgcga gaagatgacc caggcatagc cagctaatga cccctcttct g 51

<210> SEQ ID NO 24
<211> LENGTH: 27
<212> TYPE: DNA
<213> ORGANISM: Artificial
<220> FEATURE:
<223> OTHER INFORMATION: Synthetic

<400> SEQUENCE: 24
cggctaagag aaccagtgag aaagggc 27

<210> SEQ ID NO 25
<211> LENGTH: 30
<212> TYPE: DNA
<213> ORGANISM: Artificial
<220> FEATURE:
<223> OTHER INFORMATION: Synthetic

<400> SEQUENCE: 25
ccgctccctc cttcctggcc tcccgagcgg 30